US006569885B1

(12) United States Patent
Martins et al.

(10) Patent No.: US 6,569,885 B1
(45) Date of Patent: May 27, 2003

(54) CYCLIC AMP-SPECIFIC PHOSPHODIESTERASE INHIBITORS

(75) Inventors: Timothy J. Martins, Bothell, WA (US); Kerry W. Fowler, Seattle, WA (US); Carmen C. Hertel, Snohomish, WA (US); Amy Oliver, Bothell, WA (US)

(73) Assignee: Icos Corporation, Bothell, WA (US)

( * ) Notice: Subject to any disclaimer, the term of this patent is extended or adjusted under 35 U.S.C. 154(b) by 3 days.

(21) Appl. No.: 09/692,364

(22) Filed: Oct. 19, 2000

Related U.S. Application Data

(60) Provisional application No. 60/172,067, filed on Dec. 23, 1999.

(51) Int. Cl.[7] .............................................. A61K 31/415
(52) U.S. Cl. ..................... 514/403; 514/404; 514/406
(58) Field of Search ................................ 514/403, 404, 514/406

(56) References Cited

U.S. PATENT DOCUMENTS

| | | | |
|---|---|---|---|
| 4,868,198 A | | 9/1989 | Ooms et al. ............. 514/406 |
| 5,134,142 A | * | 7/1992 | Matsuo et al. ......... 514/253.09 |
| 5,434,178 A | | 7/1995 | Talley et al. ............ 514/406 |
| 5,665,754 A | | 9/1997 | Feldman et al. ........ 514/397 |
| 5,998,428 A | | 12/1999 | Barnette et al. ......... 514/285 |

FOREIGN PATENT DOCUMENTS

| | | |
|---|---|---|
| DE | 39 34 924 | 4/1991 |
| EP | 0 151 866 | 8/1985 |
| EP | 0 285 947 | 10/1988 |
| EP | 0 936 217 | 8/1999 |
| WO | WO 94/13661 | 6/1994 |
| WO | WO 95/33727 | 12/1995 |
| WO | WO 99/58523 | 11/1999 |

OTHER PUBLICATIONS

J.E. Schultz et al., *Naunyn–Schmiedeberg's Arch Pharmacol, 333*, pp. 23–30 (1986).
Z. Ma et al., *Tetrahedron: Asymmetry,* vol. 8, No. 6, pp. 883–887 (1997).
A. Robichaud et al., *Neuropharmacology, 38*, pp. 289–297 (1999).
R.A. Allen et al., *Biochemical Pharmacology,* vol. 57, pp. 1375–1382 (1999).
J. Beavo et al., "Cyclic nucleotide phosphodiesterases: Structure, regulation and drug action," Wiley and Sons, Chichester, pp. 3–14 (1990).
T.J. Torphy et al., *Drug News and Perspectives, 6*, pp. 203–214 (1993).
M.A. Giembycz et al., *Clin. Exp. Allergy, 22*, pp. 337–344 (1992).
J. Semmler et al., *Int. J. Immunopharmacol., 15*, pp. 409–413 (1993).
K.L. Molnar–Kimber et al., *Mediators of Inflammation, 1*, pp. 411–417 (1992).
M.W. Verghese et al., *J. Mol. Cell. Cardiiol., 21* (Suppl. 2), S61 (1989).
C.P. Nielson et al., *J. Allergy Immunol., 86*, pp. 801–808 (1990).
P.T. Peachell et al., *J. Immunol., 148*, pp. 2503–2510 (1992).
G. Dent et al., *J. Pharmacol., 103*, pp. 1339–1346 (1991).
S.A. Robicsek et al., *Biochem. Pharmacol., 42*, pp. 869–877 (1991).
H.S. Dhillon et al., *J. Neurotrauma, 12*, pp. 1035–1043 (1995).
N. Suttorp et al., *J. Clin. Invest., 91*, pp. 1421–1428 (1993).
M.R. Bristow et al., *Circulation, 97*, pp. 1340–1341 (1998).
G. Poli et al., *Proc. Natl. Acad. Sci. USA, 87*, pp. 782–785 (1990).
P. Orosz et al., *J. Exp. Med., 177*, pp. 1391–1398 (1993).
M. Mentz et al., *Blood, 88*, pp. 2172–2182 (1996).
S. Takeda et al., *Kidney Int., 37*, p. 362 (1990).
D. Chabardea et al., *Kidney Int., 35*, p. 494 (1989).
C.D. Nicholson, *Psychopharmacology, 101*, p. 147 (1990).
F. Eckmann et al., *Curr. Ther. Res., 43*, p 291 (1988).
A. Klodzinska et al., *Neuropharmacology, 38*, p. 1831 (1991).
H. Kato et al., *Eur. J. Pharmacol., 272*, p. 107 (1995).
G. Gardos et al., *J. Clin. Pharmocol., 16*, p. 304 (1976).
I. Shoulson et al., *Neurology, 25*, p. 722 (1975).
T. Hayakawa et al., *Clin. Exp. Pharmacol. Physiol., 26*, p. 421 (1999).
R.D. Porsolt et al., *Eur. J. Pharmacol., 47*, p. 379 (1978).
R.D. Porsolt et al., *Eur. J. Pharmacol., 57*, p. 431 (1979).
L. Steru, *Psychopharmacology, 85*, p. 376 (1985).
M. Takahashi, *J. Neuroscience, 19*, p. 610 (1999).
D. Pinsky et al., *J. Clin. Invest., 92*, pp. 2994–3002 (1993).
*Antidepressants: neurochemical, behavioral and clinical prospectives,* Enna, Malick, and Richelson, eds., Raven Press, pp. 121–139 (1981).

* cited by examiner

*Primary Examiner*—Theodore J. Criares
(74) *Attorney, Agent, or Firm*—Marshall, Gerstein & Borun

(57) ABSTRACT

Pyrazole compounds that are potent and selective inhibitors of PDE4, as well as methods of making the same, are disclosed. Use of the compounds in the treatment of inflammatory diseases and other diseases involving elevated levels of cytokines, as well as central nervous system (CNS) disorders, also is disclosed.

13 Claims, 1 Drawing Sheet

Effect of PDE 4 Inhibitors on Mouse endotoxin-stimulated TNFα Release and Spontaneous Locomotor Activity

CYCLIC AMP-SPECIFIC PHOSPHODIESTERASE INHIBITORS

CROSS-REFERENCE TO RELATED APPLICATION

This application claims the benefit of provisional application Ser. No. 60/172,067, filed Dec. 23, 1999.

FIELD OF INVENTION

The present invention relates to a series of compounds that are potent and selective inhibitors of cyclic adenosine 3',5'-monophosphate specific phosphodiesterase (cAMP specific PDE). In particular, the present invention relates to a series of novel pyrazole compounds which are useful for inhibiting the function of cAMP specific PDE, in particular, PDE4, as well as methods of making the same, pharmaceutical compositions containing the same, and their use as therapeutic agents, for example, in treating inflammatory diseases and other diseases involving elevated levels of cytokines and proinflammatory mediators.

BACKGROUND OF THE INVENTION

Chronic inflammation is a multi-factorial disease complication characterized by activation of multiple types of inflammatory cells, particularly cells of lymphoid lineage (including T lymphocytes) and myeloid lineage (including granulocytes, macrophages, and monocytes). Proinflammatory mediators, including cytokines, such as tumor necrosis factor (TNF) and interleukin-1 (IL-1), are produced by these activated cells. Accordingly, an agent that suppresses the activation of these cells, or their production of proinflammatory cytokines, would be useful in the therapeutic treatment of inflammatory diseases and-other diseases involving elevated levels of cytokines.

Cyclic adenosine monophosphate (cAMP) is a second messenger that mediates the biologic responses of cells to a wide range of extracellular stimuli. When the appropriate agonist binds to specific cell surface receptors, adenylate cyclase is activated to convert adenosine triphosphate (ATP) to cAMP. It is theorized that the agonist induced actions of cAMP within the cell are mediated predominately by the action of cAMP-dependent protein kinases. The intracellular actions of cAMP are terminated by either a transport of the nucleotide to the outside of the cell, or by enzymatic cleavage by cyclic nucleotide phosphodiesterases (PDEs), which hydrolyze the 3'-phosphodiester bond to form 5'-adenosine monophosphate (5'-AMP). 5'-AMP is an inactive metabolite. The structures of cAMP and 5'-AMP are illustrated below.

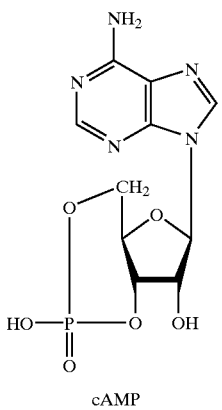

cAMP

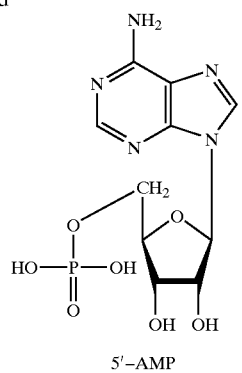

5'-AMP

Elevated levels of cAMP in human myeloid and lymphoid lineage cells are associated with the suppression of cell activation. The intracellular enzyme family of PDES, therefore, regulates the level of cAMP in cells. PDE4 is a predominant PDE isotype in these cells, and is a major contributor to cAMP degradation. Accordingly, the inhibition of PDE function would prevent the conversion of cAMP to the inactive metabolite 5'-AMP and, consequently, maintain higher cAMP levels, and, accordingly, suppress cell activation (see Beavo et al., "Cyclic Nucleotide Phosphodiesterases: Structure, Regulation and Drug Action," Wiley and Sons, Chichester, pp. 3–14, (1990)); Torphy et al., *Drug News and Perspectives*, 6, pp. 203–214 (1993); Giembycz et al., *Clin. Exp. Allergy*, 22, pp. 337–344 (1992)).

In particular, PDE4 inhibitors, such as rolipram, have been shown to inhibit production of TNFα and partially inhibit IL-1β release by monocytes (see Semmler et al., *Int. J. Immunopharmacol.*, 15, pp. 409–413 (1993); Molnar-Kimber et al., *Mediators of Inflammation*, 1, pp. 411–417 (1992)). PDE4 inhibitors also have been shown to inhibit the production of superoxide radicals from human polymorphonuclear leukocytes (see Verghese et al., *J. Mol. Cell. Cardiol.*, 21 (Suppl. 2), S61 (1989); Nielson et al., *J. Allergy Immunol.*, 86, pp. 801–808 (1990)); to inhibit the release of vasoactive amines and prostanoids from human basophils (see Peachell et al., *J. Immunol.*, 148, pp. 2503–2510 (1992)); to inhibit respiratory bursts in eosinophils (see Dent et al., *J. Pharmacol.*, 103, pp. 1339–1346 (1991)); and to inhibit the activation of human T-lymphocytes (see Robicsek et al., *Biochem. Pharmacol.*, 42, pp. 869–877 (1991)).

Inflammatory cell activation and excessive or unregulated cytokine (e.g., TNFα and IL-1β) production are implicated in allergic, autoimmune, and inflammatory diseases and disorders, such as rheumatoid arthritis, osteoarthritis, gouty arthritis, spondylitis, thyroid associated ophthalmopathy, Behcet's disease, sepsis, septic shock, endotoxic shock, gram negative sepsis, gram positive sepsis, toxic shock syndrome, asthma, chronic bronchitis, adult respiratory distress syndrome, chronic pulmonary inflammatory disease, such as chronic obstructive pulmonary disease, silicosis, pulmonary sarcoidosis, reperfusion injury of the myocardium, brain, and extremities; fibrosis, cystic fibrosis, keloid formation, scar formation, atherosclerosis, transplant rejection disorders, such as graft vs. host reaction and allograft rejection, chronic glomerulonephritis, lupus, inflammatory bowel disease, such as Crohn's disease and ulcerative oblitis, proliferative lymphocyte diseases, such as leukemia, and inflammatory dermatoses, such as atopic dermatitis, psoriasis, and urticaria.

Other conditions characterized by elevated cytokine levels include brain injury due to moderate trauma (see Dhillon et al., *J. Neurotrauma*, 12, pp. 1035–1043 (1995); Suttorp et al., *J. Clin. Invest.*, 91, pp. 1421–1428 (1993)), cardiomyopathies, such as congestive heart failure (see Bristow et al., *Circulation*, 97, pp. 1340–1341 (1998)), cachexia, cachexia secondary to infection or malignancy, cachexia secondary to acquired immune deficiency syndrome (AIDS), ARC (AIDS related complex), fever myalgias due to infection, cerebral malaria, osteoporosis and bone resorption diseases, keloid formation, scar tissue formation, and pyrexia.

In particular, TNFα has been identified as having a role with respect to human acquired immune deficiency syndrome (AIDS). AIDS results from the infection of T-lymphocytes with Human Immunodeficiency Virus (HIV). Although HIV also infects and is maintained in myeloid lineage cells, TNF has been shown to upregulate HIV infection in T-lymphocytic and monocytic cells (see Poli et al., *Proc. Natl. Acad. Sci. USA*, 87, pp. 782–785 (1990)).

Several properties of TNFα, such as stimulation of collagenases, stimulation of angiogenesis in vivo, stimulation of bone resorption, and an ability to increase the adherence of tumor cells to endothelium, are consistent with a role for TNF in the development and metastatic spread of cancer in the host. TNFα recently has been directly implicated in the promotion of growth and metastasis of tumor cells (see Orosz et al., *J. Exp. Med.*, 177, pp. 1391–1398 (1993)).

PDE4 has a wide tissue distribution. There are at least four genes for PDE4 of which multiple transcripts from any given gene can yield several different proteins that share identical catalytic sites. The amino acid identity between the four possible.catalytic sites is greater than 85%. Their shared sensitivity to inhibitors and their kinetic similarity reflect the functional aspect of this level of amino acid identity. It is theorized that the role of these alternatively expressed PDE4 proteins allows a mechanism by which a cell can differentially localize these enzymes intracellularly and/or regulate the catalytic efficiency via post translational modification. Any given cell type that expresses the PDE4 enzyme typically expresses more than one of the four possible genes encoding these proteins.

Investigators have shown considerable interest in the use of PDE4 inhibitors as anti-inflammatory agents. Early evidence indicates that PDE4 inhibition has beneficial effects on a variety of inflammatory cells such as monocytes, macrophages, T-cells of the Th-1 lineage, and granulocytes. The synthesis and/or release of many proinflammatory mediators, such as cytokines, lipid mediators, superoxide, and biogenic amines, such as histamine, have been attenuated in these cells by the action of PDE4 inhibitors. The PDE4 inhibitors also affect other cellular functions including T-cell proliferation, granulocyte transmigration in response to chemotoxic substances, and integrity of endothelial cell junctions within the vasculature.

The design, synthesis, and screening of various PDE4 inhibitors have been reported. Methylxanthines, such as caffeine and theophylline, were the first PDE inhibitors discovered, but these compounds are nonselective with respect to which PDE is inhibited. The drug rolipram, an antidepressant agent, was one of the first reported specific PDE4 inhibitors. Rolipram, having the following structural formula, has a reported 50% Inhibitory Concentration ($IC_{50}$) of about 200 nM (nanomolar) with respect to inhibiting recombinant human PDE4.

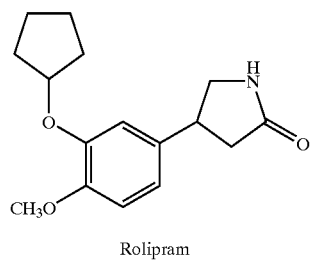

Rolipram

Investigator shave continued to search for PDE4 inhibitors that are more selective with respect to inhibiting PDE4, that have a lower $IC_{50}$ than rolipram, and that avoid the undesirable central nervous system (CNS) side effects, such as retching, vomiting, and sedation, associated with the administration of rolipram. One class of compounds is disclosed in Feldman et al. U.S. Pat. No. 5,665,754. The compounds disclosed therein are substituted pyrrolidines having a structure similar to rolipram. One particular compound, having the following structural formula, has an $IC_{50}$ with respect to human recombinant PDE4 of about 2 nM. Inasmuch as a favorable separation of emetic side effect from efficacy was observed, these compounds did not exhibit a reduction.in undesirable CNS effects.

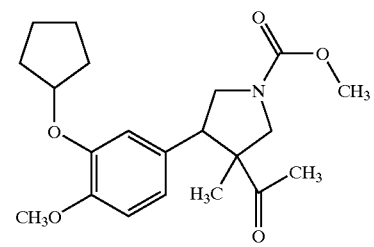

In addition, several companies are now undertaking clinical trials of other PDE4 inhibitors. However, problems relating to efficacy and adverse side effects, such as emesis and central nervous system disturbances, remain unsolved.

Accordingly, compounds that selectively inhibit PDE4, and that reduce or eliminate the adverse CNS side effects associated with prior PDE4 inhibitors, would be useful in the treatment of allergic and inflammatory diseases, and other diseases associated with excessive or unregulated production of cytokines, such as TNF. In addition, selective PDE4 inhibitors would be useful in the treatment of diseases that are associated with elevated cAMP levels or PDE4 function in a particular target tissue.

SUMMARY OF THE INVENTION

The present invention is directed t potent and selective PDE4 inhibitors useful in treatment of diseases and conditions where inhibition of PDE4 activity is considered beneficial. The present PDE4 inhibitors unexpectedly reduce or eliminate the adverse CNS side effects associated with prior PDE4 inhibitors.

In particular, the present invention is directed to pyrazole compounds having the structural formula (I):

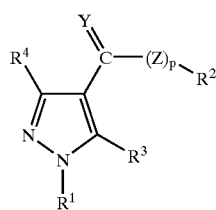

(I)

wherein
Y is O or NOH;
Z is O or NH;:
p is 0 or 1;
R¹ is selected from the group consisting of optionally substituted alkyl, cycloalkyl, aryl; heteroaryl, alkaryl, aralkyl, heteroaralkyl, and heteroalkaryl;
R² is selected from the group consisting of optionally substituted hydrogen, alkyl, cycloalkyl, aryl, heteroaryl, alkoxyalkyl, aryloxyalkyl, aralkoxyalkyl, (alkylthio)alkyl, (arylthio)alkyl, and (aralkylthio)alkyl; and
R³ and R⁴, independently, are selected from the group consisting of hydrogen, alkyl, haloalkyl, alkoxyalkyl, aryl, C(=O)alkyl, and C(=O)CH=CHNR⁵R⁶;
R⁵ and R⁶, independently, are hydrogen or alkyl, or R⁵ and R⁶ are taken together to form a 5- or 6-membered ring.

The present invention also is directed to pharmaceutical compositions containing one or more of the compounds of structural formula (I), to use of the compounds and compositions containing the compounds in the treatment of a disease or disorder, and to methods of preparing the compounds and intermediates involved in the synthesis of the compounds of structural formula (I).

DETAILED DESCRIPTION OF THE PREFERRED EMBODIMENTS

Figure 1:
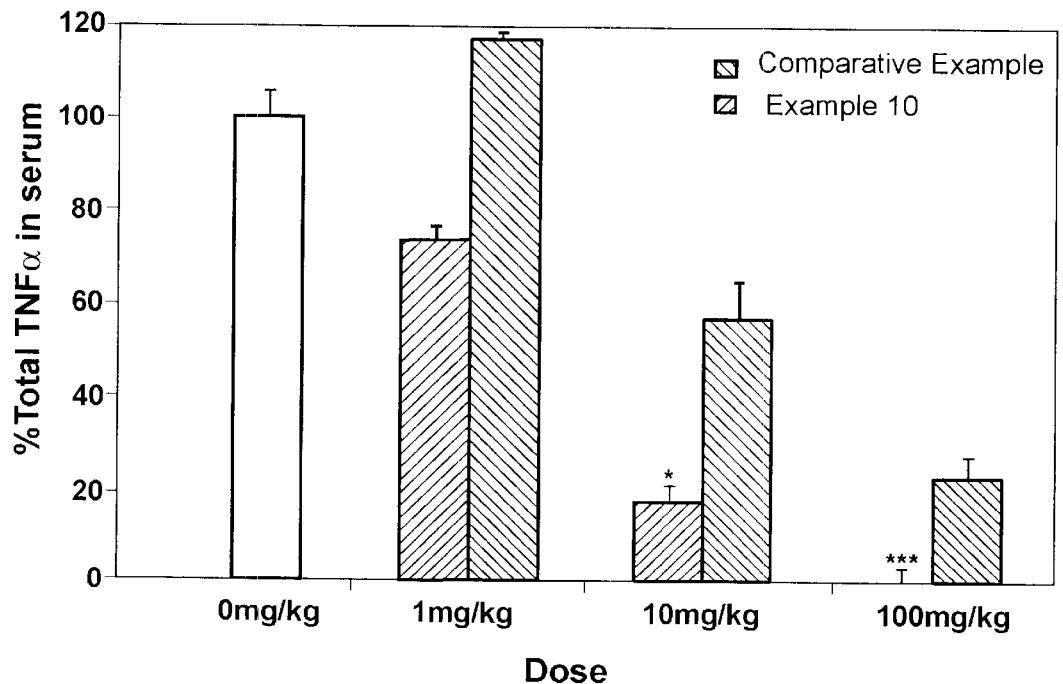
FIG. 1 contains plots of TNFα concentration in serum (pg/mL) vs. concentration of PDE4 inhibitors.

The present invention is directed to compounds having a structural formula:

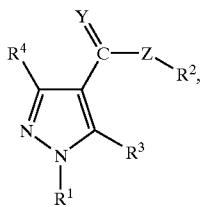

wherein
Y is O or NOH;
Z is O or NH;
R¹ is selected from the group consisting of optionally substituted alkyl, cycloalkyl, aryl, alkaryl, aralkyl, heteroaralkyl, and heteroalkaryl;
R² is selected from the group consisting of optionally substituted hydrogen, methyl, $C_{3-16}$alkyl, aryl, heteroaryl, alkoxyalkyl, aryloxyalkyl, aralkoxyalkyl, (alkylthio)alkyl, (arylthio)alkyl, and (aralkylthio)alkyl;
R³ and R⁴, independently, are selected from the group consisting of hydrogen, alkyl, haloalkyl, and aryl;

with the proviso that when R¹ is unsubstituted phenyl, R² is different from unsubstituted phenyl, unsubstituted pyridinyl, or p-tolyl.

The present invention also is directed to compounds having a structural formula:

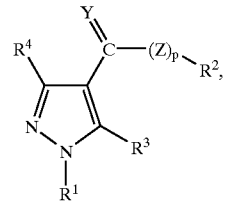

wherein
Y is O or NOH;
Z is O or NH;
p is 0 or 1;
R¹ is selected from the group consisting of alkyl, aryl, heteroaryl, alkaryl, aralkayl, heteroalkyl, and heteroalkaryl;
R² is ethyl;
R³ and R⁴, independently, are selected from the group consisting of hydrogen, alkyl, alkoxyalkyl, aryl, C(=O)alkyl, and C(=O)CH=CHNR⁵R⁶;
R⁵ and R⁶, independently, are hydrogen or alkyl, or R⁵ and R⁶ are taken together to form a 5- or 6-membered ring,
with the proviso that R¹ is different from nitro-substituted pyridinyl, amino-substituted phenyl, nitro-substituted phenyl, trichlorophenyl, and chlorotrifluorophenyl.

The present invention is further directed to compounds having a structural formula:

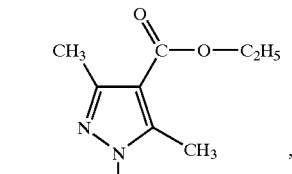

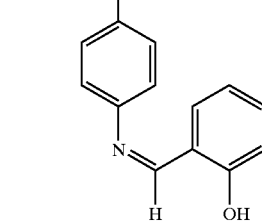

,

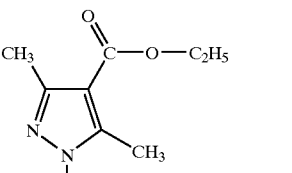

, and

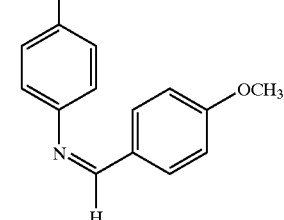

-continued

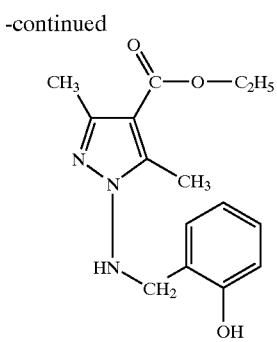

An important feature of the present invention is a method treating a disease or condition wherein inhibition of PDE activity is beneficial. The method comprises administering a therapeutically effective.amount of a compound of structural formula (I) to a mammal.

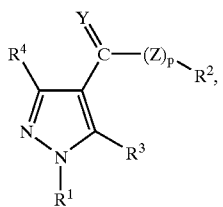

(I)

wherein
Y is O or NOH;
Z is O or NH;
p is 0 or 1;
$R^1$ is selected from the group consisting of optionally substituted alkyl, cycloalkyl, aryl, heteroaryl, alkaryl, aralkyl, heteroaralkyl, and heteroalkaryl;
$R^2$ is selected from the group consisting of optionally substituted hydrogen, alkyl, cycloalkyl, aryl, heteroaryl, alkoxyalkyl, aryloxyalkyl, aralkoxyalkyl, (alkylthio)alkyl, (arylthio)alkyl, and (aralkylthio)alkyl; and
$R^3$ and $R^4$, independently, are selected from the group consisting of hydrogen, alkyl, haloalkyl, alkoxyalkyl, aryl, C(=O)alkyl, and C(=O)CH=CHNR$^5$R$^6$;
$R^5$ and $R^6$, independently, are hydrogen or alkyl, or $R^5$ and $R^6$ are taken together to form a 5- or 6-membered ring.

A compound of structural formula (I) can be used alone, either neat or in a composition that further contains a pharmaceutically acceptable carrier. A compound of structural formula (I) also can be administered in conjunction with a second active therapeutic agent, for example, a second antiinflammatory therapeutic agent, like an agent capable of targeting TNFα.

Compounds of structural formula (I) can be used to modulate cAMP levels in a mammal, reduce TNFα levels in a mammal, suppress inflammatory cell activation in a mammal, inhibit PDE4 function in a mammal, and treat conditions in a mammal when inhibition of PDE4 provides a benefit. As used herein, the term "mammals" includes males and females, and, encompasses humans, domestic pets (e.g., cats, dogs), livestock (e.g., cattle, horses, pigs), and wildlife (e.g., primates, large felines, mammalian zoo specimens).

As used herein, the term "alkyl," alone or in combination, is defined to include straight chain and branched chain, and bridged, saturated hydrocarbon groups containing one to 16 carbon atoms. "$C_{m-n}$alkyl" refers to an alkyl group containing m to n carbon atoms. The term "lower alkyl" is defined herein as an alkyl group having one through six carbon atoms ($C_1$–$C_6$). Examples of lower alkyl groups include, but are not limited to, methyl, ethyl, n-propyl, isopropyl, isobutyl, n-butyl, nebpentyl, n-hexyl, and the like.

The term "bridged alkyl" is defined herein as a $C_6$–$C_{16}$ bicyclic or polycyclic hydrocarbon group, for example, norboryl, adamantyl, bicyclo[2.2.2]-octyl, bicyclo[2.2.1] heptyl, bicyclo[3.2.1]octyl, or decahydronaphthyl.

The term "cycloalkyl" is defined herein to include cyclic $C_3$–$C_7$ hydrocarbon groups. Examples of cycloalkyl groups include, but are not limited to, cyclopropyl, cyclobutyl, cyclohexyl, and cyclopentyl.

The term "haloalkyl" is defined herein as an alkyl group substituted with one or more halo substituents, either fluro, chloro, bromo, iodo, or combinations thereof. Similarly, "halocycloalkyl" is defined as a cycloalkyl group having one or more halo substituents.

The term "aryl," alone or in combination, is defined herein as a monocyclic-or polycyclic aromatic group, preferably a monocyclic or bicyclic aromatic group, e.g., phenyl or naphthyl, that can be unsubstituted or substituted, for example, with one or more, and in particular one to three, substituents selected from halo, alkyl, hydroxy, hydroxyalkyl, alkoxy, alkoxyalkyl, haloalkyl, nitro, amino, alkylamino, acylamino, benzenesulfonylamino, alkylthlo, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, benzenesulfonylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "aralkyl" is defined herein as a previously defined alkyl group, wherein one of the hydrogen atoms is replaced by an aryl group as defined herein, for example, a phenyl group optionally having one or more substituents, for example, halo, alkyl, alkoxy, and the like. An example of an aralkyl group is a benzyl group.

The term "alkaryl", is defined herein as a previously defined aryl group, wherein one of the hydrogen atoms is replaced by analkyl, cycloalkyl, haloalkyl, or halocycloalkyl group.

The term "heteroaralkyl" and "heteroalkaryl", are defined similarly as the term "aralkyl" and "alkaryl," however, the aryl group is replaced by a heteroaryl group as previously defined.

The term "heterocycle" or "heterocyclic ring" is defined as a 5- or 6-membered nonaromatic ring having one or more heteroatoms selected from oxygen, nitrogen, and sulfur present in the ring. Nonlimiting examples include-tetrahydrofuran, piperidine, piperazine, sulfolane, morpholine, tetrahydropyran, dioxane, and the like. A "carbocyclic ring" is similarly defined, but the ring contains solely carbon atoms.

The term "halogen" or "halo" is defined herein to include fluorine, chlorine, bromine, and iodine.

The term "alkoxy," "aryloxy," and "aralkoxyl" are defined as —OR, wherein R is alkyl, aryl, and aralkyl, respectively.

The term "alkoxyalkyl" is defined as an alkoxy group appended to an alkyl group. The terms "aryloxyalkyl" and "aralkoxyalkyl" are similarly defined as an aryloxy or aralkoxy group appended to an alkyl group. The terms "(alkylthio)alkyl," "(arylthio)alkyl," and "(aralkylthio)alkyl" are defined similarly as the three above-identified groups, except a sulfur atom, rather than an oxygen atom, is present.

The term "hydroxy" is defined as —OH.

The term "hydroxyalkyl" is defined as a hydroxy group appended to an alkyl group.

The term "amino" is defined as —NH$_2$.

The term "alkylamino" is defined as —NR$_2$ wherein at least one R is alkyl and the second R is alkyl or hydrogen.

The term "acylamino" is defined as RC(=O)NH, wherein R is alkyl or aryl.

The term "nitro" is defined as —NO$_2$.

The terms "alkylthio," "arylthio," and "aralkylthio" are defined as —SR, where R is alkyl, aryl, and aralkyl, respectively.

The term "alkylsulfinyl" is defined as R—S(Q)$_2$, where R is alkyl.

The term "alkylsulfonyl" is defined as R—S(O$_3$), where R is alkyl.

In preferred embodiments, R$^1$ is selected from the group consisting of optionally substituted alkyl, aryl, alkaryl, and heteroaryl; R$^2$ is selected from the group consisting of optionally substituted hydrogen, alkyl, and aryl; and R$^3$ and R$^4$ independently, are selected from the group consisting of optionally substituted alkyl, aryl, hydrogen, C(=O)alkyl, and C(O)CH=CHNR$^5$R$^6$.

In most preferred embodiments, R$^1$ is aryl, cycloalkyl, or heteroaryl, optionally substituted with one or more of nitro, amino, lower alkyl, alkoxy, halo, trifluoromethyl,

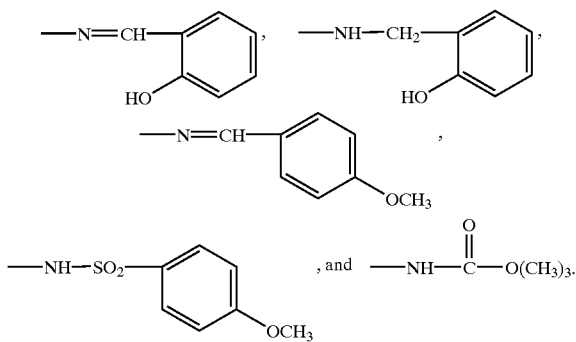

R$^1$ typically is phenyl, pyridyl, or cyclohexyl, optionally substituted.

In most preferred embodiments, R$^2$ is alkyl, hydrogen,

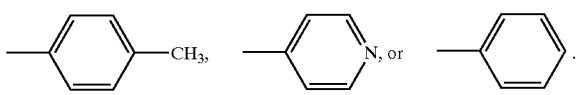

Typically, R$^2$ is ethyl, methyl, or hydrogen, p is 1, and Y and Z are O.

In most preferred embodiments, R$^3$ and R$^4$, independently, are alkyl, hydrogen, trifluoromethyl, —C(=O)CH=CHN(CH$_3$)$_2$, —C(=O)CH$_3$, or —CH$_2$OCH$_3$. Typically, R$^3$ and R$^4$ are methyl or hydrogen.

The present invention includes all possible stereoisomers and geometric isomers of compounds of structural formula (I), and includes not only racemic compounds but also the optically active isomers as well. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883–888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds. As demonstrated hereafter, specific stereoisomers exhibit an exceptional ability to inhibit PDE4 without manifesting the adverse CNS side effects typically associated with PDE4 inhibitors.

Compounds of structural formula (I) which contain acidic moieties can form pharmaceutically acceptable salts with suitable cations. Suitable pharmaceutically acceptable cations include alkali metal (e.g., sodium or potassium) and alkaline earth metal (e.g., calcium or magnesium) cations. The pharmaceutically acceptable salts of the compounds of structural formula (I), which contain a basic center, are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconatey methanesulfonate, benzenesulphonate, and p-toluenesulphonate salts. In light of the foregoing, any reference to compounds of the present invention appearing herein is intended to include compounds of structural formula (I), as well as pharmaceutically acceptable salts and solvates thereof.

The compounds of the present invention can be therapeutically administered as the neat chemical, but it is preferable to administer compounds of structural formula (I) as a.pharmaceutical composition or formulation. Accordingly, the present invention further provides for pharmaceutical formulations comprising a compound of structural formula (I), or pharmaceutically acceptable salts thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

In particular, a selective PDE4 inhibitor of the present invention is useful alone or in combination with a second antiinflammatory therapeutic agent, for example, a therapeutic agent targeting TNFα, such as ENBREL® or REMICADE®, which have utility in treating rheumatoid arthritis. Likewise, therapeutic utility of IL-1 antagonism has also been shown in animal models for rheumatoid arthritis. Thus, it is envisioned that IL-1 antagonism, in combination with PDE4 inhibition, which attenuates TNFα, would be efficacious.

The present PDE4 inhibitors are useful in the treatment of a variety of allergic, autoimmune, and inflammatory diseases.

The term "treatment" includes preventing, lowering, stopping, or reversing the progression or severity of the condition or symptoms being treated. As such, the term "treatment" includes both medical therapeutic and/or prophylactic administration, as appropriate.

In particular, inflammation is a localized, protective response elicited by injury or destruction of tissues, which serves to destroy, dilute or wall off (i.e., sequester) both the injurious agent and the injured tissue. The term "inflammatory disease," as used herein, means any disease in which an excessive or unregulated inflammatory response leads to excessive inflammatory symptoms, host tissue damage, or loss of tissue function. Additionally, the term "autoimmune disease," as used herein, means any group of disorders in which tissue injury is associated with humoral or cell-mediated responses to the body's own constituents. The term "allergic disease," as used herein, means any symptoms, tissue damage, or loss of tissue function resulting from allergy. The term "arthritic disease," as used herein, means any of a large family of diseases that are characterized by inflammatory lesions of the joints attributable to a variety of etiologies. The term "dermatitis," as used herein, means any of a large family of diseases of the skin that are characterized by inflammation of the skin attributable to a variety of etiologies. The term "transplant rejection," as used herein, means any immune reaction directed against grafted tissue (including organ and cell (e.g., bone marrow)), characterized by a loss of function of the grafted and surrounding tissues, pain, swelling, leukocytosis and thrombocytopenia.

The present invention also provides a method of modulating cAMP levels in a mammal, as well as a method of treating diseases characterized by elevated cytokine levels.

The term "cytokine," as used herein, means any secreted polypeptide that affects the functions of other cells, and that modulates interactions between cells in the immune or inflammatory response. Cytokines include, but are not limited to monokines, lymphokines, and chemokines regardless of which cells produce them. For instance, a monokine is generally referred Lo as being produced and secreted by a monocyte, however, many other cells produce monokines, such as natural killer cells, fibroblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines include, but are not limited to, interleukin-1 (IL-1), interleukin-6 (IL-6), Tumor Necrosis Factor alpha (TNFα), and Tumor Necrosis Factor beta (TNFβ).

The present invention further provides a method of reducing TNF levels in a mammal, which comprises administering an effective amount of a compound of structural formula (II) to the mammal. The term "reducing TNF levels," as used herein, means either:

a) decreasing excessive in vivo TNF levels in a mammal to normal levels or below normal levels by inhibition of the in vivo release of TNF by all cells, including but not limited to monocytes or macrophages; or b) inducing a down-regulation, at the translational or transcription level, of excessive in vivo TNF levels in a mammal to normal levels or below normal levels; or c) inducing a down-regulation, by inhibition of the direct synthesis of TNF as a postranslational event.

Moreover, the compounds of the present invention are useful in suppressing inflammatory cell activation. The term "inflammatory cell activation," as used herein, means the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules)in inflammatory cells (including but not limited to monocytes, macrophages, T lymphocytes, B lymphocytes, granulocytes, polymorphonuclear leukocytes, mast cells, basophils, eosinophils, dendritic cells, and endothelial cells). It will be appreciated by persons skilled in the art that the activation of one or a combination of these phenotypes in these cells can contribute to the initiation, perpetuation, or exacerbation of an inflammatory condition.

The compounds of the present invention also are useful in causing airway smooth muscle relaxation, bronchodilation, and prevention of bronchoconstriction.

The compounds of the present invention, therefore, are useful in treating such diseases as arthritic diseases (such as rheumatoid arthritis), osteoarthritis, gouty arthritis, spondylitis, thyroid-associated ophthalmopathy, Behcet disease, sepsis, septic shock, endotoxic shock, gram negative sepsis, gram positive sepsis, toxic shock syndrome, asthma, chronic bronchitis, allergic rhinitis, allergic conjunctivitis, vernal conjunctivitis, eosinophilic granuloma, adult (acute) respiratory distress syndrome (ARDS), chronic pulmonary inflammatory disease (such as chronic obstructive pulmonary disease), silicosis, pulmonary sarcoidosis, reperfusion injury of the myocardium, brain or extremities, brain or spinal cord injury due to minor trauma, fibrosis including cystic fibrosis, keloid formation, scar tissue formation, atherosclerosis, autoimmune diseases, such as systemic lupus erythematosus (SLE) and transplant rejection disorders (e.g., graft vs. host (GvH) reaction and allograft rejection), chronic glomerulonephritis, inflammatory bowel diseases, such as Crohn's disease and ulcerative colitis, proliferative lymphocytic diseases, such as leukemias (e.g. chronic lymphocytic leukemia; CLL) (see Mentz et al., *Blood* 88, pp. 2172–2182 (1996)), and inflammatory dermatoses, such as atopic dermatitis, psoriasis, or urticaria.

Other examples of such diseases or related conditions include cardiomyopathies, such as congestive heart failure, pyrexia, cachexia, cachexia secondary to infection or malignancy, cachexia secondary to acquired immune deficiency syndrome (AIDS), ARC (AIDS-related complex), cerebral malaria, osteoporosis and bone resorption diseases, and fever and myalgias due to infection. In addition, the compounds of the present invention are useful in the treatment of diabetes insipidus and central nervous system disorders, such as depression and multi-infarct dementia.

Compounds of the present invention also have utility outside of that typically known as therapeutic. For example, the present compounds can function as organ transplant preservatives (see Pinsky et al., *J. Clin. Invest.*, 92, pp. 2994–3002 (1993)) as well.

Selective PDE4 inhibitors also can be useful in the treatment of diabetes insipidus (*Kidney Int.*, 37, p. 362 (1990); *Kidney Int.*, 35, p. 494 (1989)) and central nervous system disorders, such as multiinfarct dementia (Nicholson, *Psychopharmacology*, 101, p. 147 (1990)), depression (Eckman et al., *Curr. Ther. Res.*, 43, p. 291 (1988)), anxiety and stress responses (*Neuropharmacology*, 38, p. 1831 (1991)), cerebral ischemia (*Eur. J. Pharmacol.*, 272, p. 107 (1995)), tardive dyskinesia (*J. Clin. Pharmocol.*, 16, p. 304 (1976)), Parkinson's disease (see *Neurology*, 25, p. 722 (1975); *Clin. Exp. Pharmacol, Physiol.*, 26, p,. 421 (1999)), and premenstrual syndrome. With respect to depression, PDE4-selective inhibitors show efficacy in a variety of animal models of depression such as the "behavioral despair" or Porsolt tests. (*Eur. J. Pharmacol.*, 47, p. 379 (1978); *Eur. J. Pharmacol.*, 57, p. 431 (1979); *Antidepressants: neurochemical, behavioral and clinical prospectives*, Enna, Malick, and Richelson, eds., Raven Press, p. 121 (1981)), and the "tail suspension test"

(*Psychopharmacology*, 85, p. 367 (1985)). Recent research findings show that chronic in vivo treatment by a variety of antidepressants increase the brain-derived expression of PDE4 (*J. Neuroscience*, 19, p. 610 (1999)). Therefore, a selective PDE4 inhibitor can be used alone or in conjunction with a second therapeutic agent in a treatment for the four major classes of antidepressants: electroconvulsive procedures, monoamine oxidase inhibitors, and selective reuptake inhibitors of serotonin or norepinephrine. Selective PDE4 inhibitors also can be useful in applications that modulate bronchodilatory activity via direct action on bronchial smooth muscle cells for the treatment of asthma.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$, with little or no toxicity The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

As appreciated by persons skilled in the art, reference herein to treatment extends to prophylaxis, as well as to treatment of established diseases or symptoms. It is further appreciated that the amount of a compound of the invention required for use in treatment varies with the nature of the condition being treated, and with the age and the condition of the patient, and is ultimately determined by the attendant physician or veterinarian. In general, however, doses employed for adult human treatment typically are in the range of 0.001 mg/kg to about 100 mg/kg per day. The desired dose can be conveniently administered in a single dose, or as multiple doses administered at appropriate intervals, for example as two, three, four or more subdoses per day. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope or the present invention.

Formulations of the present invention can be administered in a standard manner for the treatment of the indicated diseases, such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™.

For buccal administration, the composition can be in the form of tablets or lozenges formulated in conventional manner. For example, tablets and capsules for oral administration can contain conventional excipients such as binding agents (for example, syrup, accacia, gelatin, sorbitol, tragacanth, mucilage of starch or polyvinylpyrrolidone), fillers (for example, lactose, sugar, microcrystalline, cellulose, maize-starch, calciumphosphate or sorbitol), lubricants (for example,.magnesium, stearate, stearic acid, talc, polyethylene glycol or silica), disintegrants (for example, potato starch or sodium starch glycollate), or wetting agents (for example, sodium lauryl sulfate). The tablets can be coated according to methods well known in the art.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives,such as suspending agents, such as sorbitol syrup, methyl cellulose, glucose/sugar syrup, gelatin, hydroxyethylcellulose, hydroxypropylmethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsionin an acceptable oil), ion exchange resins, or as sparingly soluble derivatives (e.g., a sparingly soluble salt).

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition comprising a compound of formula (I), which process comprises mixing a compound of formula (I), together with a pharmaceutically acceptable diluent or carrier therefor.

Specific, nonlimiting examples of compounds of structural formula (I) are provided below, the synthesis of which were performed in accordance with the procedures set forth below.

Generally, compounds of structural formula (I) can be prepared according to the following synthetic scheme. In the scheme described below, it is understood in the art that protecting groups can be employed where necessary in accordance with general principles of synthetic chemistry. These protecting groups are removed in the final steps of the synthesis under basic, acidic, or hydrogenolytic conditions which are readily apparent to those skilled in the art. By employing appropriate manipulation and protection of any chemical functionalities, synthesis of compounds of structural formula (I) not specifically set forth herein can be accomplished by methods analogous to the scheme set forth below.

Unless otherwise noted, all starting materials were obtained from commercial suppliers and used without further purification. All reactions and chromatography fractions were analyzed by thin-layer chromatography on 250-mm silica gel plates, visualized with UV (ultraviolet) light and $I_2$ (iodine) stain. Flash column chromatography was carried but using Biotage 40M silica gel (230–400 mesh). Products and intermediates were purified by flash chromatography and reverse-phase HPLC.

As illustrated below, the compounds of general structural formula (I) are prepared by reacting a hydrazine of structural formula (II) with a butryric acid derivative of structural formula (III), in the presence of pyridine, in a cyclization reaction, as set forth below:

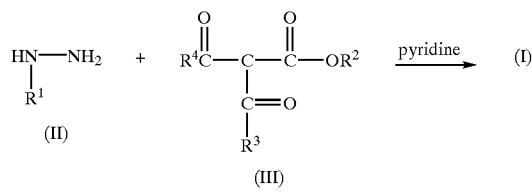

INTERMEDIATE 1

Preparation of (5-Nitropyridin-2-yl)hydrazine

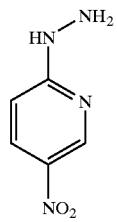

To a solution of 2-chloro-5-nitropyridine (30 mmol, 5.0 g) in absolute ethanol was added a solution of hydrazine hydrate (320 mmol, 15.8 g) in ethanol using syringe pump. At the end of the addition, the reaction was refrigerated. The named product precipitated from the reaction medium, was collected by filtration, and recrystallized from ethanol.

EXAMPLE 1

Preparation of 1-(4-Bromophenyl)-3,5-dimethyl-1H-pyrazole-4-carboxylic Acid Ethyl Ester

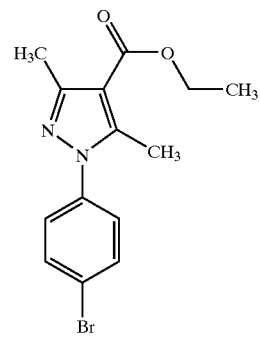

p-Bromophenylhydrazine hydrochloride (10 mmol, 2.5 g) was added to 2-acetyl-3-oxo-butyric acid ethyl ester (10 mmol, 1.7 g) in ethanol (10 mL) and pyridine (10 mL). The mixture was stirred overnight at room temperature. Thin layer chromatographic (TLC) analysis using chloroform indicated the reaction was complete. The solvents were removed under vacuum. The residue was dissolved in 150 mL ether, then washed with 50 mL water to remove the pyridine. The ether, was dried over sodium sulfate (NaSO$_4$), the solids filtered, then the solvents were removed under vacuum. The resulting oil was purified on a silica column. The named product crystallized upon standing in the column effluent, m.p. 71° C.–73° C. Analysis by $^1$H-NMR and $^{13}$C-NMR verified synthesis the named product.

EXAMPLE 2

Preparation of 3,5-Dimethyl-1-(3-nitrophenyl)-1H-pyrazole-4-carboxylic Acid Ethyl Ester

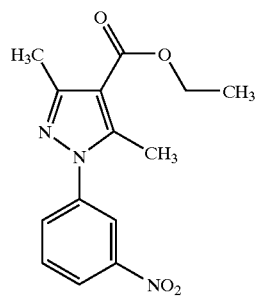

Similar to Example 1, m-nitrophenylhydrazine hydrochloride (10 mmol, 1.9 g) and 2-acetyl-3-oxo-butyric acid ethyl ester (10 mmol, 1.7 g) were mixed in a 50% solution of pyridine in ethanol. A precipitate was formed in the-reaction medium, and was collected by filtration. Analysis confirmed synthesis of the named product, m.p., 107.7° C.–109.2° C.

EXAMPLE 3

Preparation of 3,5-Dimethyl-1-phenyl-1H-pyrazole-4-carboxylic Acid Ethyl Ester

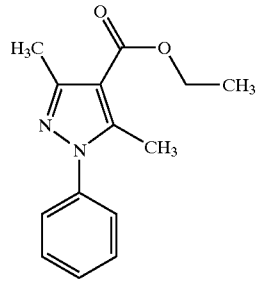

Similar to Example 1, phenyl hydrazine (7.5 mmol, 0.8 g) and 2-acetyl-3-oxo-butyric acid ethyl ester (7.5 mmol, 1.3 g) were mixed in a solution of 50% pyridine in ethanol. The solvents were removed under vacuum and the oil resuspended in chloroform. The resulting suspension was washed with 5% sodium bicarbonate, 5% hydrochloric acid, and then brine. The organic layer was dried over $NaSO_4$, the solids filtered, and the solvents removed under vacuum. The crude material was purified over silica gel to yield the named product as an oil. $^1$H-NMR ($CDCl_3$, ppm): 1.37 t (3H); 2.51 s (6H); 4.32 q (2H); 7.42 bs (5H).

EXAMPLE 4

Preparation of 3,5-Dimethyl-1-p-tolyl-1H-pyrazole-4-carboxylic Acid Ethyl Ester

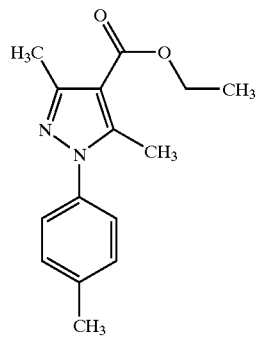

Similar to Example 1, p-tolylhydrazine (10 mmol, 1.8 g) and 2-acetyl-3-oxo-butyric acid ethyl ester (10 mmol, 1.7 g) were mixed in a solution of 50% pyridine in ethanol. The solvents were removed under vacuum. The named product was purified over silica gel (m.p. 47° C.–49° C.).

EXAMPLE 5

Preparation of 3,5-Dimethyl-1-(2-nitrophenyl)-1H-pyrazole-4-carboxylic Acid Ethyl Ester

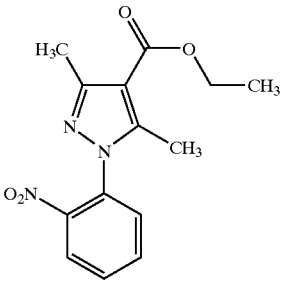

Similar to Example 1, o-nitrophenylhydrazine (20 mmol, 3.4 g) and 2-acetyl-3-oxo-butyric acid ethyl ester (20 mmol, 3.4 g) were mixed in a solution of 50% pyridine in ethanol and heated under reflux. The solvents then were removed under vacuum, and the residue was resuspended in chloroform. The resulting mixture was washed with water and dried over $NaSO_4$. The solids then were filtered, and the solvents removed under vacuum. A precipitate formed when the oily solid was dissolved in a solution of 20% hexane in chloroform. The solid was collected and discarded, and the filtrate was purified over silica gel. The named product was contaminated, then was further purified by recrystallization from ethanol to yield a solid having a melting point of 128° C.–130° C.

EXAMPLE 6

Preparation of 3,5-Dimethyl-1-(2-aminophenyl)-1H-pyrazole-4-carboxylic Acid Ethyl Ester

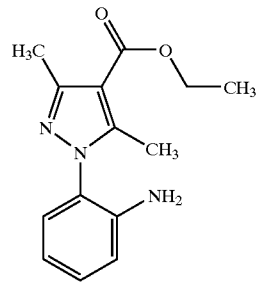

To a solution of 3,5-dimethyl-1-(2-nitrophenyl)-1H-pyrazole-4-carboxylic acid ethyl ester (0.4 g) in a solution of equal proportions of ethanol and ethyl acetate was added 5% Pd/C (37 mg). The solution was treated with hydrogen gas at 45 psi. Upon completion of the reaction, the mixture was filtered through Celite, then the filtrate concentrated under vacuum. The named product was collected as an oil, which then was purified by flash chromatography to provide a solid product having a melting point of 59° C.–61° C.

EXAMPLE 7

Preparation of 3,5-Dimethyl-1-(5-nitropyridin-2-yl)-1H-pyrazole-4-carboxylic Acid Ethyl Ester

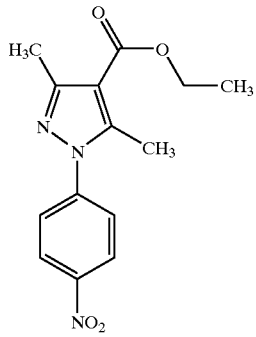

The named product was purchased from Maybridge Chemical Co., Ltd., Cornwall, UK, and used without further purification.

EXAMPLE 8

Preparation of 3,5-Dimethyl-1-pyridin-2-yl-1H-pyrazole-4-carboxylic Acid Ethyl Ester

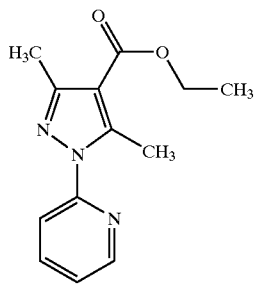

Similar to Example 1, 2-pyridylhydrazine (7.5 mmol, 0.8 g) and 2-acetyl-3-oxo-butyric acid ethyl ester (7.5 mmol, 1.3 g) were mixed in a solution of 50% pyridine in ethanol, then heated under reflux. The solvents were removed under vacuum and the residue purified over silica. The named product crystallized upon standing (m.p. 49° C.–50° C.).

EXAMPLE 9

Preparation of 1-(3-Aminophenyl)-3,5-dimethyl-1H-pyrazole-4-carboxylic Acid Ethyl Ester

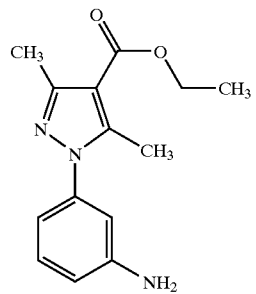

The compound of Example 2 (1.8 g,) was dissolved in ethanol then 0.2 g 5% Pd/C was added to the solution. The mixture was treated with hydrogen gas at 45 psi. Upon completion of the reaction, the solution was filtered through Celite, and the filtrate concentrated under vacuum. The named product slowly crystallized upon standing (m.p. 93° C.–95° C.).

EXAMPLE 10

Preparation of 3,5-Dimethyl-1-(3-nitropyridin-2-yl)-1H-pyrazole-4-carboxylic Acid Ethyl Ester

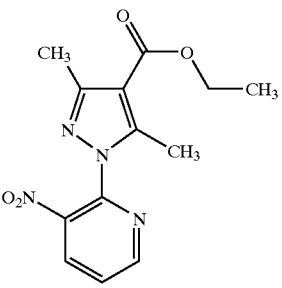

The named product was purchased from Maybridge Chemical Co., and used without further purification.

EXAMPLE 11

Preparation of 3,5-Dimethyl-1-(4-aminophenyl)-1H-pyrazole-4-carboxylic Acid Ethyl Ester

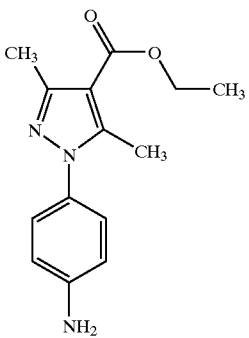

The named product was purchased from Maybridge Chemical Co., and used without further purification.

EXAMPLE 12

Preparation of 1-(3-Aminopyridin-2-yl)-3,5-dimethyl-1H-pyrazole-4-carboxylic Acid Ethyl Ester

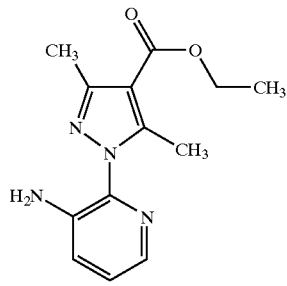

The compound of Example 10 was reduced using sodium borohydride (NaBH$_4$) (17.2 mmole) in methanol (15 ml) Following normal workup, the product was purifed over silica gel. The named product was analyzed by $^1$H-NMR (CDCl$_3$, ppm) 1.38 t (3H); 2.50 s (3H); 2.60 s (3H); 4.33 q (2H); 4.44 s (2H); 7.16 m (2H); 7.93 dd (1H).

EXAMPLE 13

Preparation of 1-[4-(4-Methoxybenzenesulfonylamino)-phenyl]-3,5-dimethyl-1H-pyrazole-4-carboxylic Acid Ethyl Ester

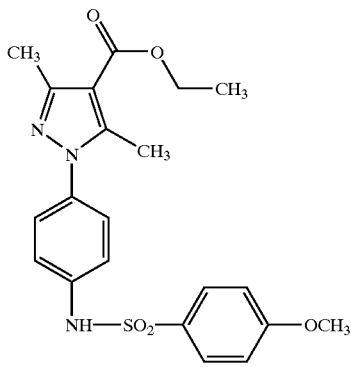

The named compound was purchased from Maybridge Chemical Co., and used without further purification.

EXAMPLE 14

Preparation of 1-[4-(2,2-Dimethylpropionylamino)-phenyl]-3,5-dimethyl-1H-pyrazole-4-carboxylic Acid Ethyl Ester

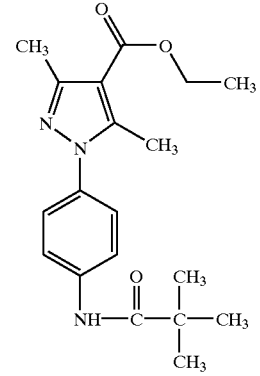

The named compound was purchased from Maybridge Chemical Co., and used without further purification.

EXAMPLE 15

3,5-Dimethyl-1-phenyl-1H-pyrazole-4-carboxylic Acid p-Tolyl Ester

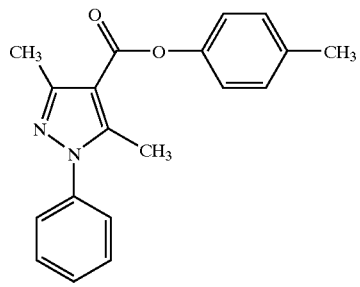

The named compound was purchased from Maybridge Chemical Co., and used without further purification.

EXAMPLE 16

Preparation of 3,5-Dimethyl-1-(3-nitropyridin-2-yl)-1H-pyrazole-4-carboxylic Acid

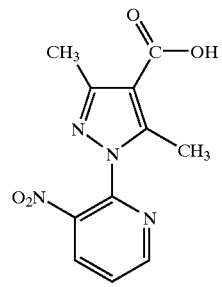

The compound of Example 10 (0.34 mmol, 0.1 g) was treated with lithium hydroxide (LiOH·H$_2$O) (0.51 mmol, 0.0219) in a 50% solution of metahnol in water at 80° C. The methanol was removed under vacuum, the resulting solution was acidified to pH 2–3, and the product extracted with ethyl acetate and dried over sodium sulfate (Na$_2$SO$_4$). The solids were removed by filtration, and solvents removed under vacuum. The resulting solid was used without further purification, and $^1$H-NMR analysis determined the solid to be the named compound $^1$H-NMR (CDCl$_3$, ppm): 2.48 s (3H); 2.76 s (3H); 7.58 dd (1H); 7.32 dd (1H); 8.76 dd (1H).

EXAMPLE 17

Preparation of 3,5-Dimethyl-1-(5-nitropyridin-2-yl)-1H-pyrazole-4-carboxylic Acid Ethyl Ester

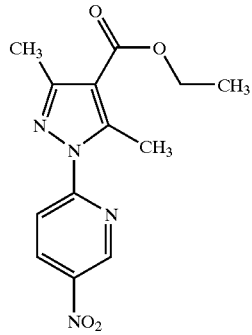

Similar to Example 1, equimolar amounts of (5-nitropyridin-2-yl)hydrazine and 2-acetyl-3-oxo-butyric acid ethyl ester were combined in a solution of 50% pyridine in ethanol. Analysis confirmed synthesis of the named product (m.p. 117° C.–119° C.).

EXAMPLE 18

Preparation of 1-(4-Aminophenyl)-3,5-dimethyl-1H-pyrazole-4-carboxylic Acid

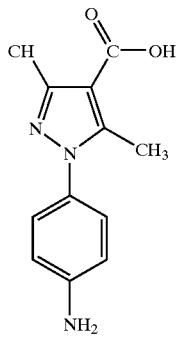

Similar to Example 16, the compound of Example 11 (0.38 mmol, 0.1 g) was treated with LiOH.H$_2$O (0.57 mmol, 0.024 g) in a 50% solution of methanol in water. The resulting solid was determined to be the named compound by $^1$H-NMR (CDCl$_3$, ppm): 2.46 sd (3H); 2.57 s (2H); 2.75 sd (3H); 7.85 dd (2H); 8.42 dd (2H).

EXAMPLE 19

Preparation of 1-Cyclohexyl-3,5-dimethyl-1H-pyrazole-4-carboxylic Acid Ethyl Ester

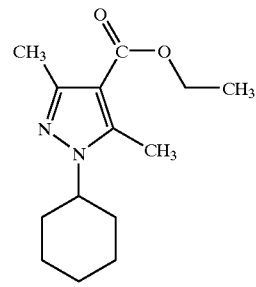

Similar to Example 1, equimolar amounts of cyclohexyl hydrazine hydrochloride and 2-acetyl-3-oxobutyric Acid Ethyl Ester were combined in a solution of 50% pyridine in ethanol. Analysis confirmed synthesis of the named product (m.p. 66° C.–67° C.).

EXAMPLE 20

Preparation of 1-Benzyl-3,5-dimethyl-1H-pyrazole-4-carboxylic Acid Ethyl Ester

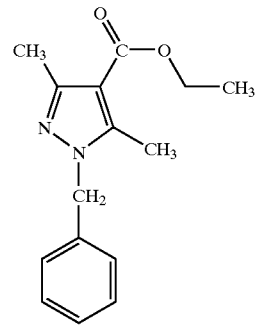

Similar to Example 1, equimolar amounts of benzylhydrazine dihydrochloride and 2-acetyl-3-oxo-butyric acid ethyl ester were combined in a solution of 50% pyridine in ethanol. The resulting oil was determined to be the named product by $^1$H-NMR (CDCl$_3$, ppm): 1.35 t (3H); 2.44 s (3H); 2.45 s (3H); 4.38 a (2H); 5.25 s (2H); 7.08 d (2H); 7.29 m (3H).

EXAMPLE 21

Preparation of 1-(3-Chlorophenyl)-3,5-dimethyl-1H-pyrazole-4-carboxylic Acid Ethyl Ester

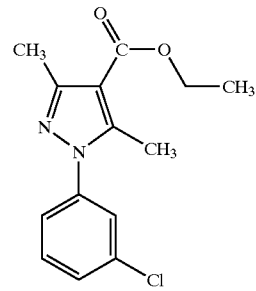

Similar to Example 1, equimolar amounts of 3-chlorophenylhydrazine hydrochloride and 2-acetyl-3-oxobutyric acid ethyl ester were combined in a solution of 50% pyridine in ethanol. Analysis confirmed that the resulting solid was determined to be the named product (m.p. 56° C.–57° C.).

EXAMPLE 22

Preparation of 3,5-Dimethyl-1-m-tolyl-1H-pyrazole-4-carboxylic Acid Ethyl Ester

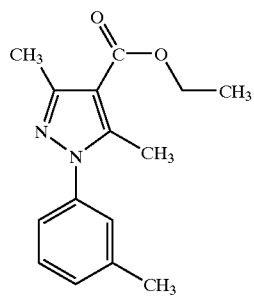

Similar to Example 1, equimolar amounts of m-tolylhydrazine hydrochloride and 2-acetyl-3-oxo-butyric acid ethyl ester were combined in a solution of a 50% pyridine in ethanol. The resulting oil was purified by flash chromatography to yield the named product as a solid (m.p. 46.5° C.–47.5° C.).

EXAMPLE 23

Preparation of 1-(3-Fluorophenyl)-3,5-dimethyl-1H-pyrazole-4-carboxylic Acid Ethyl Ester

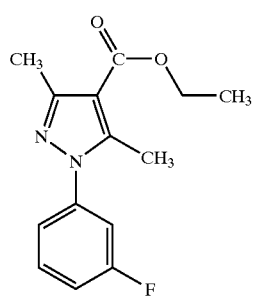

Similar to Example 1, equimolar amounts of 3-fluorophenylhydrazine hydrochloride and 2-acetyl-3-oxo-butyric acid ethyl ester were combined in a solution of 50% pyridine in ethanol. Analysis showed that resulting solid was the named product (m.p. 55° C.–56.1° C.).

EXAMPLE 24

Preparation of 1-(3-Methoxyphenyl)-3,5-dimethyl-1H-pyrazole-4-carboxylic Acid Ethyl Ester

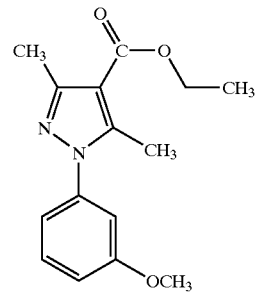

Similar to Example 1, equimolar amounts of 3-methoxyphenylhydrazine hydrochloride and 2-acetyl-3-oxo-butyric acid ethyl ester were combined in a Solution of 50% pyridine in ethanol. The resulting solid was determined to be the named product by $^1$H-NMR (CDCl$_3$, ppm): 1.38 t (3H); 2.50 s (3H); 2.52 s (3H); 3.84 s (3H); 4.32 q (2H); 6.96 m (3H); 7.3 st (1H).

EXAMPLE 25

Preparation of 1-(3-Broomophenyl)-3,5-dimethyl-1H-pyrazole-4-carboxylic Acid Ethyl Ester

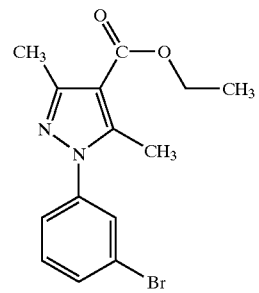

Similar to Example 1, equimolar amounts of 3-bromophenylhydrazine hydrochloride and 2-acetyl-3-oxo-butyric acid ethyl ester were combined in a solution of 50% pyridine in ethanol. Analysis showed that the resulting solid was the named product (m.p. 34° C.–35° C.).

EXAMPLE 26

Preparation of 3-Methyl-1-pyridin-2-yl-1H-pyrazole-4-carboxylic Acid Ethyl Ester

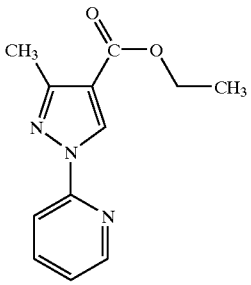

Similar to Example 1, equimolar amounts of 2-pyridylhydrazine and 2-formyl-3-oxo-butyric acid ethyl ester were combined in a solution of 50% pyridine in ethanol. Analysis showed that the resulting solid was determined to be the named product (m.p. 49° C.–50° C.).

EXAMPLE 27

Preparation of 1-(4-Aminophenyl)-5-trifluoromethyl-1H-pyrazole-4-carboxylic Acid Ethyl Ester

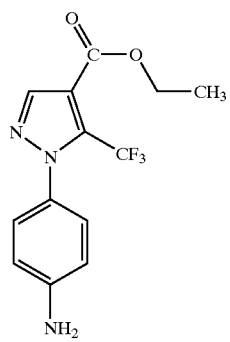

To 1-(4-nitrophenyl)-5-trifluoromethyl-1H-pyrazole-4-carboxylic acid ethyl ester (0.5 g, 1.5 mmol) dissolved in methanol (4 mL) was added palladium on carbon and ammonium formate (0.428 g, 6.8 mmol). This mixture was stirred at room temperature overnight. The solvent was removed under vacuum, then the material was resuspended in chloroform, and washed with water (twice) and saturated sodium bicarbonate (once), and the organic layer dried over magnesium sulfate ($MgSO_4$). The solid was filtered and the solvents removed under vacuum. The reaction product was purified over silica gel to yield the named product (m.p. 102° C.–103° C.).

The following Examples 28–37 were purchased from Maybridge Chemical Co., Ltd. (Exs. 29, 30, 32–37), ACROS Organics, Pittsburgh, Pa. (Ex. 28), or Bionet Research Ltd., Cornwall, UK (Ex. 31), and used without further purification.

EXAMPLE 28

3,5-Dimiethyl-1-phenyl-1H-pyrazole-4-carboxaldehyde

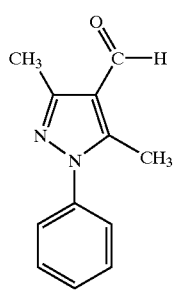

EXAMPLE 29

5-(3-Dimethylaminoacryloyl)-1-(6-methyl-4-trifluoromethylpyridin-2-yl)-1H-pyrazole-4-carboxylic Acid Methyl Ester

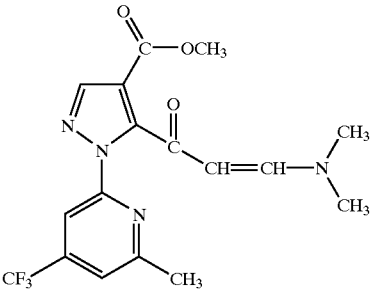

EXAMPLE 30

1-(4-Nitrophenyl)-5-trifluoromethyl-1H-pyrazole-4-carboxylic Acid Ethyl Ester

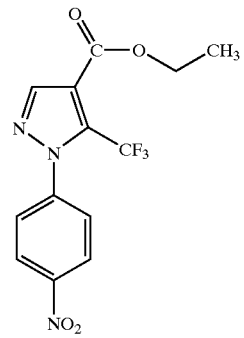

EXAMPLE 31

1-(3-Chloro-5-trifluoromethylpyridin-2-yl)-5-methyl-1H-pyrazole-4-carboxylic Acid Ethyl Ester

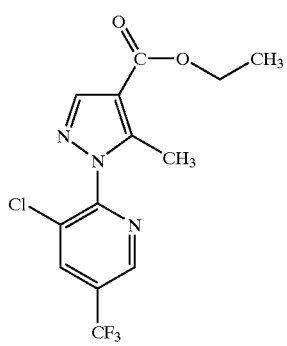

EXAMPLE 32

1-[5-Methyl-1-(6-methyl-4-trifluoromethyl-pyridin-2-yl)-1H-pyrazol-4-yl]-ethanone Oxime

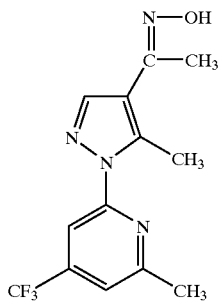

EXAMPLE 33

5-Acetyl-1-(6-methyl-4-trifluoromethylpyridin-2-yl)-1H-pyrazole-4-carboxylic Acid Methyl Ester

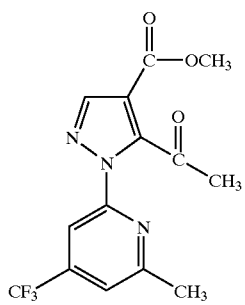

EXAMPLE 34

3,5-Dimethyl-1-phenyl-1H-pyrazole-4-carboxylic Acid Pyridin-4-ylamide

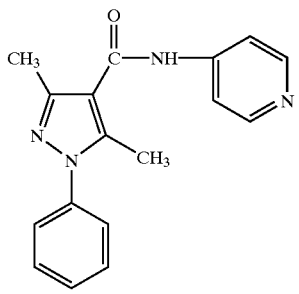

EXAMPLE 35

5-Methoxymethyl-1-(2,4,6-trichlorophenyl)-1H-pyrazole-4-carboxylic Acid Ethyl Ester

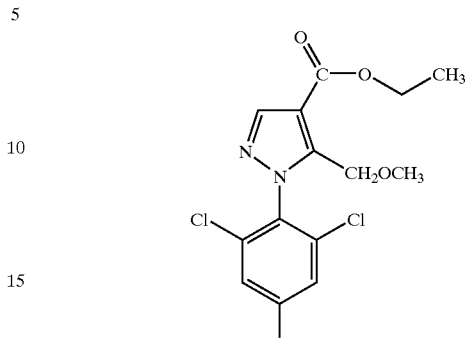

EXAMPLE 36

3,5-Dimethyl-1-phenyl-1H-pyrazole-4-carboxylic Acid Phenylamide

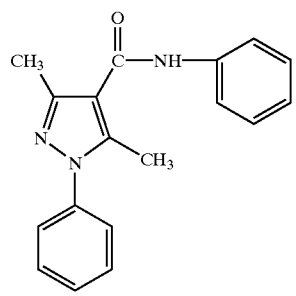

EXAMPLE 37

5-Acetyl-1-pyridin-2-yl-1H-pyrazole-4-carboxylic Acid Methyl Ester

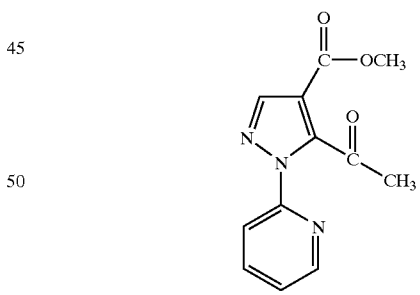

The compounds of structural formula (I) were tested for an ability to inhibit PDE4. The ability of a compound to inhibit PDE4 activity is related to the $IC_{50}$ value for the compound, i.e., the concentration of inhibitor required for 50% inhibition of enzyme activity. The $IC_{50}$ value for compounds of structural formula (I) were determined using human recombinant PDE4.

The compounds of the present invention typically exhibit an $IC_{50}$ value against recombinant human PDE4 of less than about 100 $\mu$M, and preferably less than about 50 $\mu$M, and more preferably less than about 25 $\mu$m. The compounds of the present invention typically exhibit an $IC_{50}$ value against recombinant human PDE4 of less than about 10 µM, and often less than about 1 µM. To achieve the full advantage of the present invention, a present PDE4 inhibitor has an $IC_{50}$ of about 0.05 µM to about 25 µM.

The $IC_{50}$ values for the compounds were determined from concentration-response curves typically using concentrations ranging from 0.1 µM to 500 µM. Tests against other PDE enzymes using standard methodology, as described in Loughney et al., *J. Biol. Chem.*, 271, pp. 796–806 (1996), also showed that compounds of the present invention are highly selective for the cAMP-specific PDE4 enzyme.

In particular, a compound of the present invention, i.e., Example 2, has an $IC_{50}$ vs. human recombinant PDE4B of 0.1 µM, but has an $IC_{50}$ vs. PDE1A of 25.1 µM, vs. PDE1B of 25.7 µM, vs. PDE1C of 30.2 µM, vs. PDE2 of 21.8 µM, vs. PDE3A of 137 µM, vs. PDE5 of 25.6 µM, and vs. PDE7 of 39 µM. This illustrates the selectivity of the present compound with respect to inhibiting PDE4.

The compounds of structural formulae (I) and (II) were tested for an ability to reduce TNFα secretions in human peripheral blood lymphocytes. The ability of a compound to reduce TNFα secretion is related to the $EC_{50}$ value for the compound (i.e., the effective concentration of the compound capable of inhibiting 50% of the total TNFα).

The compounds of the present invention typically exhibit an $EC_{50}$ value of less than about 50 µM, and preferably less than about 20 µM, and more preferably less than about 15 µm. The compounds of the present invention preferably exhibit a PBL/TNFα $EC_{50}$ value of less than about 10 µM, and often less than about 5 µM. To achieve the full advantage of the present invention, a present PDE4 inhibitor has an $EC_{50}$ of about 0.01 µM to about 15 µM.

The production of recombinant human PDEs and the $IC_{50}$ and $EC_{50}$ determinations can be accomplished by well-known methods in the art. Exemplary methods are described as follows:

EXPRESSION OF HUMAN PDEs

Expression in Baculovirus-Infected *Spodoptera fugiperda* (*Sf9*) Cells

Baculovirus transfer plasmids were constructed using either pBlueBacIII (Invitrogen) or pFastBac (BRL-Gibco). The structure of all plasmids was verified by sequencing across the vector junctions and by fully sequencing all regions generated by PCR. Plasmid pBB-PDE1A3/6 contained the complete open reading frame of PDE1A3 (Loughney et al., *J. Biol. Chem.*, 271, pp. 796–806 (1996)) in pblueBacIII. Plasmid Hcam3aBB contained the complete open reading frame of PDE1C3 (Loughney et al. (1996)) in pBlueBacIII. Plasmid pBB-PDE3A contained the complete open reading frame of PDE3A (Meacci et al., *Proc. Natl. Acad. Sci., USA*, 89, pp. 3721–3725 (1992)) in pBlueBacIII.

Recombinant virus stocks were produced using either the MaxBac system (Invitrogen) or the FastBac system (Gibco-BRL) according to the manufacturer's protocols. In both cases, expression of recombinant human PDEs in the resultant viruses was driven off the viral polyhedron promoter. When using the MaxBac® system, virus was plaque purified twice in order to insure that no wild type (occ+) virus contaminated the preparation. Protein expression was carried out as follows. *Sf*9 cells were grown at 27° C. in Grace's Insect culture medium (Gibco-BRL) supplemented with 10% fetal bovine serum, 0.33% TC yeastolate, 0.33% lactalbumin hydrolysate, 4.2 mM $NaHCO_3$, 100 µg/mL gentamycin, 100 units/mL penicillin, and 100 µg/mL streptomycin. Exponentially growing cells were infected at a multiplicity of approximately 2 to 3 virus particles per cell and incubated for 48 hours. Cells were collected by centrifugation, washed with nonsupplemented Grace's medium, and quick-frozen for storage.

Expression in *Saccharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium-containing glycerol was added to a final concentration of 2×YET/3% glycerol. Approximately 24 hr later, cells were harvested, washed, and stored at −70° C.

CALMODULIN PURIFICATION

Calmodulin used for activation of the PDE1 enzymes was purified from bovine testes essentially as described by Dedman et al., *Methods in Enzymology*, 102, pp. 1–8 (1983) using the Pharmacia Phenyl-Sepharose® procedure.

IMMOBILIZATION OF CALMODULIN ON AGAROSE

Calmodulin was immobilized on BioRad Affi-Gel® 15 per manufacturer's instructions.

HUMAN PHOSPHODIESTERASE PREPARATIONS

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 µL reaction mixture containing (final concentrations) 40 mM Tris HCl (pH 8.0), 1 µM $ZnSO_4$, 5 mM $MgCl_2$, and 0.1 mg/mL bovine serum albumin (BSA) Alternatively, in assays assessing PDE1-specific activity, incubation mixtures further incorporated the use of 0.1 mM $CaCl_2$ and 10 kg/mL calmodulin. PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) µg of *Crotalus atrox* venom then was added, and the incubation was continued for 3 minutes (15 minutes total). The reaction was stopped by addition of 200 µL of activated charcoal (25 mg/mL suspension in 0.1 M $NaH_2PO_4$, pH 4).

After centrifugation (750×g for 3 minutes) to sediment the charcoal, a sample of the supernatant was taken for radioactivity determination in a scintillation counter and the PDE activity was calculated.

Inhibitor analyses were performed similarly to the method described in Loughney et al., *J. Biol. Chem.*, 271, pp. 796–806 (1996), except both cGMP and cAMP were used, and substrate concentrations were kept below 32 nM, which is far below the Km of the tested PDE5. cl Purification of PDE1A3 from SF9 Cells Cell pellets (5 g) were mixed with 10 mL of Lysis Buffer (50 mM MOPS pH 7.5, 2 mM dithiothreitol (DTT), 2 mM benzamidine HCl, 5 μM $ZnSO_4$, 0.1 mM $CaCl_2$, 20 kg/mL calpain inhibitors I and II, and 5 μg/mL each of leupeptin, pepstatin, and aprotinin) at room temperature. The cells were lysed by passage through a French® pressure cell (SLM-Aminco®, Spectronic Instruments, Inc., Rochester N.Y.). The resultant lysate was centrifuged in a Beckman ultracentrifuge using a type T180 rotor at 45,000 rpm for 1 hr. The supernatant was recovered and filtered through a 0.2 μm filter. This filtrate was applied to a 2.6×90 cm column of SEPHACRYL® S-300 equilibrated in Column Buffer A (Lysis Buffer containing 100 mM NaCl, and 2 mM $MgCl_2$). The column flow rate was adjusted to 1 mL/min and fractions of 7 mL were collected. Active fractions were pooled and supplemented with 0.16 mg of calmodulin. The enzyme was applied overnight at a flow rate of 0.2 mL/min to an ACC-1 agarose immunoaffinity column as described in Hansen et al., *Methods in Enzymology* 159, pp, 453–557 (1988). The column was washed with 5 volumes of Column Buffer B (Column Buffer A without NaCl) and followed by 5 volumes of Column Buffer C (Column Buffer A containing 250 mM NaCl). The column was eluted with Column Buffer D (50 mM MOPS pH 7.5, 1 mM EDTA, 1 mM EGTA, 1 mM DTT, 1 mM benzamidine HCl, 100 mM NaCl, 20 μg/mL calpain inhibitors I and II, and 5 μg/mL each of leupeptin, pepstatin, and aprotinin) by applying one column volume at 0.1 mL/min, stopping flow for 1 hour, and then continuing elutionat the same flow rate. Fractions of 0.5 mL were collected. Fractions displaying activity were pooled, and first dialyzed against dialysis buffer containing 25 mM MOPS pH 7.5, 100 mM NaCl, 10 μM $ZnSO_4$, 1 mM $CaCl_2$, 1 mM DTT, and 1 mM benzamidine HCl. A subsequent dialysis against dialysis buffer containing 50% glycerol was performed prior to quick freezing the sample with dry ice and storage at −70° C. The resultant preparations were about 10 to 15% pure by SDS-PAGE. These preparations had specific activities of about 5 to 20 kmol cAMP hydrolyzed per minute per milligram protein.

Purification of PDE1B from *S. cerevisiae*

Yeast cells (50 g) were thawed by mixing with 100 mL glass beads (0.5 mM, acid washed) and 200 mL Buffer A at room temperature. Buffer A consisted of 50 mM MOPS pH 7.5, 1 mM DTT, 2 mM benzamidine HCl, 0.01 mM $ZnSO_4$, 5 mM $MgCl_2$, 20 μg/mL calpain inhibitors I and II, and 5 μg/mL each of leupeptin, pepstatin, and aprotinin. The mixture was cooled to 4° C., transferred to a Bead-Beater®, and the cells lysed by rapid mixing for 6 cycles of 30 seconds each. The homogenate was centrifuged for 15 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE1B was precipitated by the addition of solid ammonium sulfate (0.33 g/mL, supernatant) while stirring in an ice bath and maintaining the pH between 7.0 and 7.5. This mixture then was centrifuged for 22 minutes in a Beckman J2 centrifuge using a JA-10 rotor at 9,00.0 rpm (12,000×g). The supernatant was discarded and the pellet was dissolved in 100 mL of buffer B (50 mM MOPS pH 7.5, 1 mM DTT, 1 mM benzamidine HCl, 0.01 mM $ZnSO_4$, 2 mM $MgCl_2$, 2 mM $CaCl_2$, and 5 μg/mL each of leupeptin, pepstatin, and aprotinin). The pH and conductivity were corrected to 7.5 and 15–20 millisiemens (mS), respectively. This solution was loaded onto a 20 mL column of calmodulin-Agarose that had been equilibrated with 10 column volumes of Buffer B at a rate of 1 mL/min. The flow-through was reapplied to the column at least 5 times. The column was washed with 5 volumes of Buffer B, 5 volumes of buffer B containing 250 mM NaCl, and 2 volumes of Buffer B without NaCl again. Elution was accomplished by applying one volume of Buffer C (50 mM MOPS pH 7.5, 1 mM EDTA, 1 mM EGTA, 1 mM DTT, 1 mM benzamidine HCl) at 0.33 mL/min, then stopping flow for 1 hour before continuing the elution. Fractions of about 4 mL were collected and assayed for PDE activity. Active fractions were pooled and concentrated to a volume of 5 mL, using an Amicon ultrafiltration system. The concentrate was then applied to a 320 mL Sephacryl® S-300 column (1.6× 150 cm) that had been equilibrated with at least 2'volumes of Buffer D (25 mM MOPS pH 7.5, 1 mM DTT, 1 mM benzamidine HCl, 0.01 mM $ZnSO_4$, 2 mM $CaCl_2$, and 100 mM NaCl). The column was developed at a flow rate of 1 mL/min (11 cm/hr), and 5 mL fractions were collected. The activity peak was pooled and dialyzed overnight against Buffer D containing 50% glycerol. The purified enzyme was frozen on dry ice and stored at −70° C. The resultant preparations were about >90% pure by SDS-PAGE. These preparations had specific activities of about 10 to 30 μmol cGMP hydrolyzed per minute per milligram protein.

Purification of PDE1C3 from *Sf*9 Cells

Cell pellets (5 g) were thawed on ice with 20 mL of Lysis Buffer (50 mM MOPS pH 7.4, 10 μM $ZnSO_4$, 0.1 mM $CaCl_2$, 1 mM DTT, 2 mM benzamidine HCl, 5 μg/mL each of pepstatin, leupeptin, and aprotinin). Cells were lysed by passage through a French® pressure cell (SLM-Aminco®, Spectronic Instruments) while temperatures were maintained below 10° C. The resultant cell homogenate was centrifuged at 36,000 rpm at 4° C. for 45 min in a Beckman ultracentrifuge using a Type TI45 rotor. The supernatant was discarded and the resultant pellet was resuspended with 40 mL of Solubilization Buffer (Lysis Buffer containing 1 M NaCl, 0.1 M $MgCl_2$, 1 mM $CaCl_2$, 20 μg/mL calmodulin, and 1% Sulfobetaine SB12 (Z3-12) by sonicating using a VibraCell tuner with a microtip for 3×30 seconds. This was performed in a crushed ice/salt mix for cooling. Following sonication, the mixture was slowly mixed for 30 minutes at 4° C. to finish solubilizing membrane bound proteins. This mixture was centrifuged in a Beckman ultracentrifuge using a type TI45 rotor at 36,000 rpm for 45 minutes. The supernatant was diluted with Lysis Buffer containing 10 μg/mL calpain inhibitors I and II. The precipitated protein was centriluged for 20 minutes at 9,000 rpm in a Beckman JA-10 rotor. The recovered supernatant then was subjected to Mimetic Blue® AP Agarose Chromatography.

To run the Mimetic Blued AP Agarose Column, the resin initially was shielded by the application of 10 bed volumes of 1% polyvinylpyrrolidone (i.e., MW of 40,000) to block nonspecific binding sites. The loosely bound PVP-40 was removed by washing with 10 bed volumes of 2 M NaCl, and 10 mM sodium citrate pH 3.4. Just prior to addition of the solubilized PCE1C3 sample, the column was equilibrated with 5 bed volumes of Column Buffer A (50 mM MOPS pH 7.4, 10 $\mu$M ZnSO$_4$, 5 mM MgCl$_2$, 0.1 mM CaCl$_2$, 1 mM DTT, 2 mM benzamidine HCl).

The solubilized sample was applied to the column at a flow rate of 2 mL/min with recycling such that the total sample was applied 4 to 5 times in 12 hours. After loading was completed, the column was washed with 10 column volumes of Column Buffer A, followed by 5 column volumes of Column Buffer B (Column Buffer A containing 20 mM 5'-AMP), and followed by 5 column volumes of Column Buffer C (50 mm MOPS pH 7.4, 10 $\mu$M ZNSO$_4$, 0.1 mM CaCl$_2$, 1 mM DTT, and 2 mM benzamidine HCl). The enzyme was eluted into three successive pools. The first pool consisted of enzyme from a 5-bed volume wash with Column Buffer C containing 1 mM cAMP. The second pool consisted of enzyme from a 10-bed volume wash with Column Buffer C containing 1 M NaCl. The final pool of enzyme consisted of a 5-bed volume wash with Column Buffer C containing 1 M NaCl and 20 mM cAMP.

The active pools of enzyme were collected and the cyclic nucleotide removed via conventional gel filtration chromatography or chromatography on hydroxyapatite resins. Following removal of cyclic nucleotides, the enzyme pools were dialyzed against Dialysis Buffer containing 25 mM MOPS pH 7.4, 10 $\mu$M ZnSO$_4$, 500 mM NaCl, 1 mM CaCl$_2$, 1 mM DTT, 1 mM benzamidine HCl, followed by dialysis against Dialysis buffer containing 50% glycerol. The enzyme was quick-frozen with the aid of dry ice and stored at −70° C.

The resultant preparations were about >90% pure by SDS-PAGE. These preparations had specific activities of about 0.1 to 1.0 $\mu$mol cAMP hydrolyzed per minute per milligram protein.

Purification of PDE2 from *S. cerevisiae*

Frozen yeast cell pellets from strain YI34 (10 g, stored at −70° C.) were allowed to thaw on ice in 25 mL of Lysis Buffer (50 mM MOPS, pH 7.2, 1 mM EDTA, 1 mM EGTA, 0.1 mM DTT, 0.1 mM 4-(2-amino-ethyl)benzenesulfonyl fluoride (AEBSF), 1 $\mu$g/mL of pepstatin, leupeptin, aprotinin, calpain inhibitors I and II, and 2 mM benzamidine). Cells were lysed by three passages through a French® pressure cell (SLM-Aminco®, Spectronic Instruments). The lysate was centrifuged at 36,000 rpm in a Beckman Ultracentrifuge rotor Type 45Ti for 60 minutes at 4° C. The supernatant was separated from sediment and passed through a 15 mL Epoxy-cGMP Sepharos® resin at 4° C. two times at about 0.5 mL/min. The column subsequently was washed with 45 mL of Wash Buffer 1 (50 mM MOPS, pH 7.2, 0.1 mM EDTA, 0.1 mM DTT). Following this wash, the column was washed with 45 mL of Wash Buffer 2 (Wash-Buffer 1 containing-0.5 M NaCl). Following this salt wash, the column was washed with 15 mL of Wash Buffer 3 (Wash Buffer 1 containing 0.25 M NaCl). The column was transferred to room temperature and allowed to warm. Approximately 25 mL of Elution Buffer (Wash Buffer 3 containing 10 mM cGMP, maintained at room temperature) was applied to the column and the effluent was collected in 2 mL fractions. Small aliquots of each of the fractions were diluted 20-fold in PBS containing 5 mM MgCl$_2$ to allow hydrolysis of the competing ligand and to aid detection of PDE2 activity. Active fractions were passed through a Pharmacia PD-100 gel filtration column to exchange into Wash Buffer 3. This exchanged pool was diluted 50% v/v with sterile 80% glycerol and stored at −20° C. The resultant preparations were greater than 85% pure as judged by SDS-PAGE with subsequent staining of protein by Coomassie R-250. These preparations had specific activities of about 150 to 250 $\mu$mol cGMP hydrolyzed per minute per milligram protein.

Preparation of PDE3A from *Sf9* Cells

Cells (2×1010) were suspended in Lysis Buffer containing 50 MM MOPS pH 7.5, 2 mM DTT, 2 mM benzamidine HCl, 5 $\mu$M ZnSO$_4$, 0.1 mM CaCl$_2$, 20 $\mu$g/mL calpain inhibitors I and II, and 5 $\mu$g/mL each of leupeptin, pepstatin, and aprotinin. The mixture was sonicated twice for 30 seconds and the cells were lysed in a French® pressure cell (SLM-Aminco®, Spectronic Instruments) at 4° C. The lysate was centrifuged 100,000×g for 45 minutes. The pellet was washed once in Lysis Buffer and suspended in 46 mL Lysis Buffer with a Dounce homogenizer. Aliquots were stored at −70° C. These preparations had specific activities of about 1 to 2 nmol cAMP hydrolyzed per minute per milligram protein.

HUMAN PDE4A, 4B, 4C, 4D PREPARATIONS

Preparation of PDE4A from *S. cerevisiae*

Yeast cells (50 g of yeast strain YI26 harboring HDUN1.46) were thawed at room temperature by mixing with 50 mL of Lysis Buffer (50 mM MOPS pH 7.5, 10 $\mu$M ZnSO$_4$, 2 mM MgCl$_2$, 14.2 mM 2-mercapto-ethanol, 5 $\mu$g/mL each of pepstatin, leupeptin, aprotinin, 20 $\mu$g/mL each of calpain inhibitors I and II, and 2 mM benzamidine HCl). Cells were lysed in a French® pressure cell (SLM-Aminco®, Spectronic Instruments) at 10° C. The extract was centrifuged in a Beckman JA-10 rotor at 9,000 rpm for 22 minutes at 4° C. The supernatant was removed and centrifuged in a Beckman TI45 rotor at 36,000 rpm for 45 minutes at 4° C.

PDE4A was precipitated from the high-speed supernatant by the addition of solid ammonium sulfate (0.26 g/mL supernatant) while stirring in an ice bath and maintaining the pH between 7.0 and 7.5.. The precipitated proteins containing PDE4A were collected via centrifugation in a Beckman JA-10 rotor at 9,000 rpm for 22 minutes. The precipitate was resuspended in 50 mL of Buffer G (50 $\mu$M MOPS pH 7.5, 10 $\mu$M ZnSO$_4$, 5 mM MgCl$_2$, 100 mM NaCl, 14.2 mM 2-mercaptoethanol, 2 mM benzamidine HCl, 5 $\mu$g/mL each of leupeptin, pepstatin, and aprotinin, and 20 $\mu$g/mL each of calpain inhibitors I and II) and passed through a 0.45 $\mu$m filter.

The resuspended sample (50 to 100 mL) was loaded onto a 5×100 cm column of Pharmacia SEPHACRYL® S-300 equilibrated in Buffer G. Enzyme activity was eluted at a flow rate of 2 mL/min and pooled for later fractionation.

The PDE4A isolated from gel filtration chromatography was applied to a 1.6×20 cm column of Sigma Cibacron Blue Agarose-type 300 (10 mL) equilibrated in Buffer A (50 mM MOPS pH 7.5, 10 $\mu$M ZnSO$_4$, 5 mM MgCl$_2$, 14.2 mM 2-mercaptoethanol, and 100 mM benzamidine HCl). The column was washed in succession with 50 to 100 mL of Buffer A, 20 to 30 mL of Buffer A containing 20 mM 5'-AMP, 50 to 100 mL of Buffer A containing 1.5 M NaCl, and 10 to 20 mL of Buffer C (50 mM Tris HCl pH 8, 10 $\mu$M ZnSO$_4$, 14.2 mM 2-mercaptoethanol, and 2 mM benzamidine HCl). The enzyme was eluted with 20 to 30 mL of Buffer C containing 20 mM cAMP.

The PDE activity peak was pooled, and precipitated with ammonium sulfate (0.33 g/mL enzyme pool) to remove excess cyclic nucleotide. The precipitated proteins were resuspended in Buffer X (25 mM MOPS pH 7.5, 5 µM ZnSO$_4$, 50 mM NaCl, 1 mM DTT, and 1 mM benzamidine HCl), and desalted via gel filtration on a Pharmacia PD-10® column per manufacturer's instructions. The enzyme was quick-frozen in a dry ice/ethanol bath and stored at −70° C.

The resultant preparations were about >80% pure by SDS-PAGE. These preparations had specific activities of about 10 to 40 µmol cAMP hydrolyzed per minute per milligram protein.

Preparation of PDE4B from *S. cerevisiae*

Yeast cells (150 g of yeast strain YI23 harboring HDUN2.32) were thawed by mixing with 100 mL glass beads (0.5 mM, acid washed) and 150 mL Lysis Buffer (50 mM MOPS pH 7.2, 2 mM EDTA, 2 mM EGTA, 1 mM DTT, 2 mM benzamidine HCl, 5 µg/mL each of pepstatin, leupeptin, aprotinin, calpain inhibitors I and II) at room temperature. The mixture was cooled to 4° C., transferred to a Bead-Beater®, and the cells lysed by rapid mixing for 6 cycles of 30 seconds each. The homogenate was-centrifuged for 22 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE4B was precipitated by the addition of solid ammonium sulfate (0.26 g/mL supernatant) while stirring in an ice bath and maintaining the pH between 7.0 and 7.5. This mixture was then centrifuged for 22 minutes in a Beckman J2 centrifuge using a JA-10 rotor at 9,000 rpm (12,000×g). The supernatant was discarded and the pellet was dissolved in 200 mL of Buffer A (50 mM MOPS pH 7.5, 5 mM MgCl$_2$, 1 mM DTT, 1 mM benzamidine HCl, and 5 µg/mL each of leupeptin, pepstatin, and aprotinin). The pH and conductivity were corrected to 7.5 and 15–20 mS, respectively.

The resuspended sample was loaded onto a 1.6×200 cm column (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5M NaCl, and 25 to 50 mL of Buffer A. The enzyme was eluted with 50 to 75 mL of Buffer E (50 mM Tris HCl pH 8, 2 mM EDTA, 2 mM EGTA, 1 mM DTT, 2 mM benzamidihe HCl, and 20 mM cAMP) and 50 to 75 mL of Buffer E containing 1 M NaCl. The PDE activity peak was pooled, and precipitated with ammonium sulfate (0.4 g/mL enzyme pool) to remove excess cyclic nucleotide. The precipitated proteins were resuspended in Buffer X (25 mM MOPS pH 7.5, 5 µM ZnSO$_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme was quick-frozen in a dry ice/ethanol bath and stored at −70° C.

The resultant preparations were about >90% pure by SDS-PAGE. These preparations had specific activities of about 10 to 50 µmol cAMP hydrolyzed per minute per milligram protein.

Preparation of PDE4C from *S. cerevisiae*

Yeast cells (150 g of yeast strain YI30 harboring HDUN3.48) were thawed by mixing with 100 mL glass beads (0.5 mM, acid washed) and 150 mL Lysis Buffer (50 mM MOPS pH 7.2, 2 mM EDTA, 2 mM EGTA, 1 mM DTT, 2 mM benzamidine HCl, 5 µg/mL each of pepstatin, leupeptin, aprotinin, calpain inhibitors I and II) at room temperature. The mixture was cooled to 4° C., transferred to a BEAD-BEATER®, and the cells lysed by rapid mixing for 6 cycles of 30 sec each. The homogenate was centrifuged for 22 minutes in a Beckman J2-21M centrifuge using a JA-10 rotor at 9,000 rpm and 4° C. The supernatant was recovered and.centrifuged in a Beckman XL-80 ultracentrifuge using a TI45 rotor at 36,000 rpm for 45 minutes at 4° C.

The supernatant was recovered and PDE4C was precipitated by the addition of solid ammonium sulfate (0.26 g/mL supernatant) while stirring in an ice bath and maintaining the pH between 7.0 and 7.5. Thirty minutes later, this mixture was centrifuged for 22 minutes in a Beckman J2 centrifuge-using a JA-10 rotor at 9,000 rpm (12,000×g). The supernatant was discarded and the pellet was dissolved in 200 mL of Buffer A (50 mM MOPS pH 7.5, 5 mM MgCl$_2$, 1 mM DTT, 2 mM benzamidine HCl, and 5 µg/mL each of leupeptin, pepstatin, and aprotinin). The pH and conductivity were corrected to 7.5 and 15–20 mS, respectively.

The resuspended sample was loaded onto a 1.6×20 cm column (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5 M NaCl, and then 25 to 50 mL of Buffer A. The enzyme was.eluted with 50 to 75 mL of Buffer E (50 mM Tris HCl pH 8, 2 mM EDTA, 2 mM EGTA, 1 mM DTT, 2 mM benzamidine HCl, and 20 mM cAMP) and 50 to 75 mL of Buffer E containing 1 M NaCl. The PDE4C activity peak was pooled, and precipitated with ammonium sulfate (0.4 g/mL enzyme pool) to remove excess cyclic nucleotide. The precipitated proteins were resuspended in Buffer X (25 mM MOPS pH 7.2, 5 µM ZnSO$_4$, 50 mM NaCl, 1 mM DTT, and 1 mM benzamidine HCl) and desalted via gel filtration on a Pharmacia PD-100 column per manufacturer's instructions. The enzyme pool was dialyzed overnight against Buffer X containing 50% glycerol. This enzyme was quick-frozen in a dry ice/ethanol bath and stored at −70° C.

The resultant preparations were about >80% pure by SDS-PAGE. These preparations had specific activities of about 10 to 20 µmol cAMP hydrolyzed per minute per milligram protein.

Preparation of PDE4D from *S. cerevisiae*

Yeast cells (100 g of yeast strain YI29 harboring HDUN4.11) were thawed by mixing with 150 mL glass beads (0.5 mM, acid washed) and 150 mL Lysis Buffer (50 mM MOPS pH 7.2, 10 µM ZnSO$_4$, 2 mM MgCl$_2$, 14.2 mM 2-mercaptoethanol, 2 mM benzamidine HCl, 5 µg/mL each of pepstatin, leupeptin, aprotinin, calpain inhibitors I and II) at room temperature. The mixture was cooled to 4° C., transferred to a Bead-Beater®, and the cells lysed by rapid mixing for 6 cycles of 30 sec each. The homogenate was centrifuged for 22 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE4D was precipitated by the addition of solid ammonium sulfate (0.33 g/mL supernatant) while stirring in an ice bath and maintaining the pH between 7.0 and 7.5. Thirty minutes later, this mixture was centrifuged for 22 minutes in a Beckman J2 centrifuge using a JA-10 rotor at 9,000 rpm (12,000×g). The supernatant was discarded and the pellet was dissolved in 100 mL of Buffer A (50 mM MOPS pH 7.5, 10 µM ZnSO$_4$, 5 mM MgCl$_2$, 14.2 mM 2-mercaptoethanol, 100 mM benzamidine HCl, and 5 ||g/mL each of leupeptin, pepstatin, aprotinin, calpain inhibitor I and II). The pH and conductivity were corrected to 7.5 and 15–20 mS, respectively.

At a flow rate of 0.67 mL/min, the resuspended sample was loaded onto a 1.6×20 cm column (10 mL) of Sigma Cibacron Blue Agarose-type 300 equilibrated in Buffer A. The column was washed in succession with 50 to 100 mL of Buffer A, 20 to 30 mL of Buffer A containing 20 mM 5'-AMP, 50 to 100 mL of Buffer A containing 1.5 M NaCl, and then 10 to 20 mL of Buffer C (50 mM Tris HCl pH 8, 10 4 μM ZnSO$_4$, 14.2 mM 2-mercaptoethanol, 2 mM benzamidine HCl). The enzyme was eluted with 20 to 30 mL of Buffer C containing 20 mM cAMP.

The PDE4D activity peak was pooled and precipitated with ammonium sulfate (0.4 g/mL enzyme pool) to remove excess cyclic nucleotide. The precipitated proteins were resuspended in Buffer X (25 mM MOPS pH 7.2, 5 μM ZnSO$_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme preparation was quick-frozen in a dry ice/ethanol bath and stored at −70° C.

The resultant preparations were about >80% pure by SDS-PAGE. These preparations had specific activities of about 20 to 50 μmol cAMP hydrolyzed per minute per milligram protein.

Purification of PDE5 from S. cerevisiae

Cell pellets (29 g) were thawed on ice with an equal volume of Lysis Buffer (25 mM Tris HCl, pH 8, 5 mM MgCl$_2$, 0.25 mM DTT, 1 mM benzamidine, and 10 μM ZnSO$_4$). Cells were lysed in a Microfluidizer (Microfluidics Corp.) using nitrogen at 20,000 psi. The lysate was centrifuged and filtered through 0.45 μm disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 mM MgCl$_2$, 0.25 mM DTT, 10 μM ZnSO$_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM MgCl$_2$, 0.25 mM DTT, 10 μM ZnSO$_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 μM ZnSO$_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 μmol cGMP hydrolyzed per minute per milligram protein.

Preparation of PDE7 from S. cerevisiae

Cell pellets (126 g) were thawed and resuspended at room temperature for about 30 minutes with an equal volume of Lysis Buffer (50 mM Tris HCl, pH 8, 1 mM EDTA, 1 mM DTT, 50 mM NaCl, 2 mM benzamidine HCl, and 5 μg/mL each of pepstatin, leupeptin, and aprotinin). The cells were lysed at 0–4° C. with the aid of glass beads (125 mL) in a Bead-Beater® for 6×30 second cycles. The lysate was centrifuged and filtered through 0.45 μm disposable filters. The filtered extract (178 mL) was distributed into 4 mL aliquots, quick-frozen with dry ice, and stored in a freezer at −70° C. These preparations were stable to several cycles of freezing and thawing and had specific activities of about 50 to 100 pmol cAMP hydrolyzed per minute per mlligram protein.

Lipopolysaccharide-Stimulated TNFα Release from Human Peripheral Blood Lymphocytes To assess the ability of a compound to reduce TNFα secretion in human peripheral blood lymphocytes (PBL), the following tests were performed. Previous studies have demonstrated that incubation of human PBL with cAMP-elevating agents, such as prostaglandin E21 forskolin, 8-bromo-cAMP, or dibutryl-cAMP, inhibits the secretion of TNFα by the cells when stimulated by lipopolysaccharide (LPS; endotoxin). Accordingly, preliminary experiments have been performed to.demonstrate that selective PDE4 inhibitors, such as rolipram, inhibit LPS-induced TNFα secretion from human lymphocytes in a dose-dependent fashion. Hence, TNFα secretion from human PBL was used as a standard for the ability of a compound to elevate intracellular cAMP concentrations and/or to inhibit PDE4 activity within the cell.

Heparinized blood (approximately 30 mL) drawn from human volunteers was mixed 1:1 with Dulbecco's modified phosphate-buffered saline. This mixture was mixed 1:1 with HISTOPAQUE® and centrifuged at 1,500 rpm at room temperature without braking in the swinging bucket of a Beckman model TJ6 centrifuge. Erythrocytes were centrifuged to the bottom of the tubes, and serum remained at the surface of the tubes. A layer containing lymphocytes sedimented between the serum and HISTOPAQUE® layers, and was removed by aspiration to a fresh tube. The cells were quantified and adjusted to 3×10$^6$ cells/ml and a 100 μL aliquot is placed into the wells of a 96 well plate. Test compounds and RPMI media (Gibco/BRL Life Sciences) are added to each of the wells 15 minutes prior to addition of bacterial LPS (25 mg/mL). The mixture was allowed to incubate for 20 hours at 37° C. in a humidified chamber. The cells then were separated by centrifuging at 800 rpm for 5 minutes at room temperature. An aliquot of 180 μL of supernatant was transferred to a new plate for determination of TNFα concentration. TNFα protein in the cell supernatant fluids was measured using a commercially available enzyme-linked immunosorbent assay (ELISA) (CYTOSCREEN® Immunoassay Kit from Biosource International).

The cell-based assay provided the following results for various compounds of the present invention. The EC$_{50}$ values (i.e., effective concentration of the compound capable of inhibiting 50% of the total TNFα) illustrate the ability of the present compounds to inhibit LPS-stimulated TNFα release from human PBL.

The following summarizes the IC$_{50}$ values determined for compounds of structural formula (I) against human recombinant PDE4. In the following table, R$^3$ and R$^4$ are both methyl, Y and Z are O, and p is 1, unless otherwise noted.

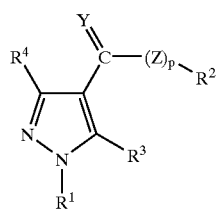
| Example | R¹ | R² | PDE4 IC$_{50}$ ($\mu$M) |
|---|---|---|---|
| 19 | cyclohexyl | Et | .053 |
| 2 | C$_6$H$_4$NO$_2$ (3-nitrophenyl) | Et | 0.10 |
| 10 | C$_5$H$_3$N$_2$O$_2$ (3-nitropyridin-2-yl) | Et | 0.20 |
| 11 | C$_5$H$_6$N (4-aminophenyl) | Et | 0.30 |
| 3 | C$_6$H$_5$ | Et | 0.31 |
| 38 | C$_{13}$H$_{10}$NO | Et | 0.40 |

-continued

| Example | R¹ | R² | PDE4 IC₅₀ (μM) |
|---|---|---|---|
| 5 | 2-nitrophenyl (C₆H₄NO₂) | Et | 0.65 |
| 39 | 4-methylphenyl-N=CH-(4-methoxyphenyl) (C₁₄H₁₂NO) | Et | 0.69 |
| 40 | 4-methylphenyl-NH-CH₂-(2-hydroxyphenyl) (C₁₃H₁₂NO) | Et | 0.92 |
| 12 | 3-amino-2-methylpyridinyl (C₅H₅N₂) | Et | 0.94 |
| 9 | 3-aminophenyl (C₆H₆N) | Et | 1.03 |

-continued
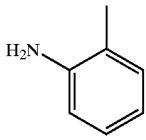
| Example | R¹ | R² | PDE4 IC$_{50}$ ($\mu$M) |
|---|---|---|---|
| 6 | 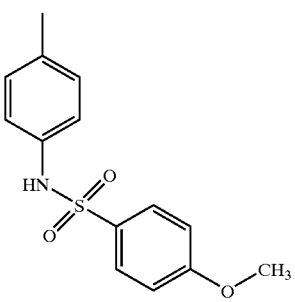<br>C$_6$H$_6$N | Et | 1.13 |
| 13 | 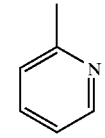<br>C$_{13}$H$_{12}$NO$_3$S | Et | 1.88 |
| 26 | 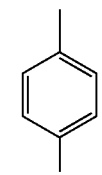<br>C$_5$H$_4$N | Et<br>(R³ = H) | 3.59 |
| 27 | 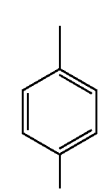<br>C$_6$H$_6$N | Et<br>(R³ = CF$_3$)<br>(R⁴ = H) | 3.61 |
| 4 | <br>C$_7$H$_7$ | Et | 3.94 |

-continued

[Structure: pyrazole with R¹ on N, R³ at 5-position, R⁴ at 3-position, and C(=Y)-(Z)p-R² at 4-position]

| Example | R¹ | R² | PDE4 IC₅₀ ($\mu$M) |
|---|---|---|---|
| 1 | 4-bromophenyl (C$_6$H$_4$Br) | Et | 4.76 |
| 14 | 4-(2-methyl-2-methylpropanamido)phenyl (C$_{11}$H$_{14}$NO) | Et | 6.39 |
| 7 | 4-nitrophenyl (C$_6$H$_4$NO$_2$) | Et | 12.88 |
| 28 | phenyl (C$_6$H$_5$) | H (p = 0) | 18.02 |
| 15 | phenyl (C$_6$H$_5$) | 4-methylphenyl (CH$_3$) | 36.50 |

-continued

[Structure: pyrazole with R¹ on N1, R³ on C5, R⁴ on C3, and C(=Y)-(Z)p-R² on C4]

| Example | R¹ | R² | PDE4 IC$_{50}$ ($\mu$M) |
|---|---|---|---|
| 29 | 2,6-dimethyl-4-(trifluoromethyl)pyridin-3-yl (C$_7$H$_5$NF$_3$) | Me (R³ = $\overset{O}{\overset{\|}{C}}$CH=CHN(CH$_3$)$_2$) (R⁴ = H) | 36.95 |
| 30 | 4-nitrophenyl (C$_6$H$_4$NO$_2$) | Et (R³ = CF$_3$) (R⁴ = H) | 45.37 |
| 16 | 3-nitro-2-methylpyridin-? (C$_5$H$_3$N$_2$O$_2$) | H | 47.40 |
| 17 | 5-nitro-2-methylpyridin-? (C$_5$H$_3$N$_2$O$_2$) | Et | 57.45 |
| 31 | 3-chloro-2-methyl-5-(trifluoromethyl)pyridin-? (C$_6$H$_2$NClF$_3$) | Et (R⁴ = H) | 63.05 |
| 32 | 2,6-dimethyl-4-(trifluoromethyl)pyridin-3-yl (C$_7$H$_5$NF$_3$) | Me (Y = NOH) (R⁴ = H) (p = 0) | 67.42 |

-continued
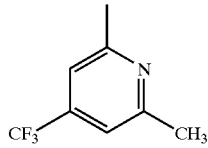
| Example | R¹ | R² | PDE4 IC$_{50}$ ($\mu$M) |
|---|---|---|---|
| 33 | 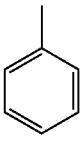<br>C$_7$H$_5$NF$_3$ | Me<br>(R³ = C(=O)CH$_3$)<br>(R⁴ = H) | 88.21 |
| 34 | 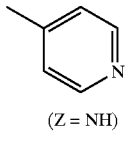<br>C$_6$H$_5$ | 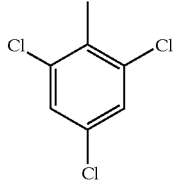<br>(Z = NH) | 97.91 |
| 35 | 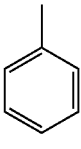<br>C$_6$H$_2$Cl$_3$ | Et<br>(R³ = CH$_2$OCH$_3$)<br>(R⁴ = H) | 130.92 |
| 36 | 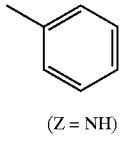<br>C$_6$H$_5$ | 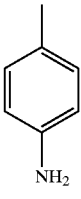<br>(Z = NH) | 141.96 |
| 18 | 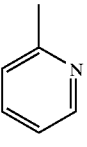<br>C$_6$H$_6$N | H | 174.93 |
| 37 | <br>C$_6$H$_4$N | Me<br>(R³ = C(=O)CH$_3$)<br>(R⁴ = H) | 180.67 |
Et is ethyl
Me is methyl The data presented above shows that compounds of formula (I) are potent and selective inhibitors of PDE4, e.g., the compounds have an $IC_{50}$ vs. human recombinant PDE4 of about 0.1 to about 180 μM. As an important added advantage, the compounds of formula (I): reduced or eliminated the adverse side effects, such as CNS effects and emesis, associated with prior PDE4 inhibitors. In particular, compounds of formula (I) were tested in cell-based assays and in animal models to illustrate the efficacy of the compounds with respect to inhibiting PDE4 both in vitro and in vivo.

The cell-based assay provided the following results for various pyrazole compounds of the present invention. The $EC_{50}$ values (i.e., effective concentrations of the compound capable of inhibiting 50% of the total TNFα) illustrate the ability of the present compounds to inhibit LPS-stimulated TNFα release from human peripheral blood lymphocytes.

| Compound | PDE4 $IC_{50}$ (μM) | PBL/TNFα $EC_{50}$ (μM) |
| --- | --- | --- |
| Example 19 | 0.053 | 0.52 |
| Example 10 | .20 | 2.0 |
| Example 11 | .30 | 1.0 |
| Example 3 | .31 | 1.8 |
| Example 38 | .40 | 1.0 |
| Example 39 | .69 | 1.3 |
| Example 40 | .92 | 6.2 |
| Example 12 | .94 | 2.6 |
| Example 9 | 1.0 | 1.9 |

The above table illustrates the ability of compounds of formula (I) to inhibit PDE4 activity and TNFα release. Preferred compounds have a PBL/TNFα $EC_{50}$ about 50 nM or less, and preferably about 20 nM or less. More preferred compounds have a PBL/TNFα $EC_{50}$ of 15 nM or less.

To achieve the full advantages of the present invention, the compound has an $IC_{50}$ vs. human recombinant PDE4 of about 100 nM or less and a PBL/TNFα $EC_{50}$ of about 50 nM or less. More preferably, the compound has an $IC_{50}$ of about 50 nM or less and a PBL/TNFα $EC_{50}$ of about 10 nM or less.

ANIMAL MODELS

Assay for Inhibition of Serum TNFα Levels in Mammals (Mouse/TNFα $ED_{50}$ (mg/kg))

In order to assess the ability of a compound to reduce serum TNFα levels in mammals, the following protocol was employed. Those skilled in the art appreciate that previous studies have demonstrated that incubation of LPS-activated human monocytes with agents that can elevate cAMP, like PGE2, forskolin, and the dbcAMP, inhibited secretion of TNFα. PDE4 inhibitors like rolipram, which also elevate cAMP, have been found to inhibit serum TNFα as well. Rolipram has also been found to inhibit secretion of TNFα from LPS-activated mouse macrophages. Accordingly, in vivo efficacy of a PDE4 reducing compound was shown by dosing with compound and measuring reduction of serum TNFα levels in LPS-injected mice. Female C3H mice, 20–25 gm body weight, were fasted overnight and dosed intraperitoneally with test compound in appropriate vehicle 60 minutes before LPS injection. Five μg of LPS was then injected intraperitoneally into the mice. Ninety minutes after LPS injection, mice were bled from the heart. Blood was allowed to clot overnight at 4° C. Samples were centrifuged for 10 minutes in a microcentrifuge and the serum removed and stored at −20° C. until analysis. Serum levels of TNFα were subsequently measured using a commercially available ELISA kit (Genzyme) following the protocol enclosed in the kit. The inhibition of serum TNFα levels caused by the compound was determined relative to serum TNFα levels in control mice receiving vehicle alone. The results are summarized in the plots of FIG. 1.

Combined Mouse Endotoxin-Stimulated TNFα Release and Locomotor Activity Assay ($ED_{50}$ (mg/kg))

The purpose of this study was to determine the efficacy of PDE4 inhibitors in vivo in an LPS mouse model together with a determination with respect to central nervous system (CNS) side-effects manifested by a decrease in spontaneous mobility.

The test animals were female Balb/c mice, having an average weight of about 20 g. The PDE4 inhibitors, formulated in 30% Cremophor® EL, were administered via intraperitoneal (i.p.) injections at doses of 0.1, 1.0, 10.0, and 100 mg/kg. Individual dose volumes (about 150 μL) were adjusted based on the body weights measured. One hour later, 5 mg/kg LPS in a final volume of 200 μL was injected via the tail vein to each animal. Ninety minutes following the LPS treatment, the animals were bled and serum samples were collected before being stored at −70° C. until assayed.

For efficacy determination, the serum samples were diluted two-fold and TNFα levels were determined using the CYTOSCREEN® Immunoassay Kit (Biosource International). The data were averaged between triplicate sample subjects for each of the tested compounds.

For side-effect profiling, a subjective visual scoring system was utilized at 5 min and 20 min after administration of PDE4 inhibitors. Vehicle control animals were rated a single "+" and animals that were effectively immobilized and stretched out on the bottom of the cage with little detectable movement were rated as "++++." Alternatively, a semi-automated "open field" system (e.g., a Photobeam Activity Measurement System as sold by San Diego Instruments) for monitoring movements was used for assessing the effect of PDE4 inhibitors on mice and/or rats. In this instance, the subjects could number of "light-beam" crosses per unit of time. A decrease in the number of activity events is directly proportional to the mobility or immobilization of the animal. The quantitative scoring correlated well with the subjective measurements described above.

| Compound | Vehicle control | 1 mg/kg | 10 mg/kg | 100 mg/kg |
| --- | --- | --- | --- | --- |
| Comparative Example[1] | | 3 | 3 | 3 |
| Example 2 | 3 | 3 | 3 | 3 |

[1] trans-3-(3-cyclopentoxy-4-methoxyphenyl)-1-methoxycarbonyl-4-methyl-4-(methylcarbonyl)pyrrolidine, i.e., Example 12 of Feldman et al. U.S. Pat. No. 5,665,754, incorporated herein by reference.

| Compound No. | Doses (mg/kg) | Sedative Effect | % TNFα Inhibition |
| --- | --- | --- | --- |
| Comparative Example | 1 | — | 43 |
| | 10 | + | 100 |
| | 100 | +++ | 100 |
| Example 2 | 1 | — | — |
| | 10 | — | 70 |
| | 100 | — | 100 |

The data presented above show that compounds of formula (I) are potent and selective inhibitors of PDE4. As an important added advantage, the compounds of formula (I) also reduced or eliminated the adverse CNS side effects associated with prior PDE4 inhibitors. Compounds of formula (I) were further tested for emetogenic properties in animal models to further illustrate the efficacy of the compounds. The method and results of the emetogenic test are set forth below.

The results show that the compounds of the present invention are useful for selectively inhibiting PDE4 activity in a mammal, without exhibiting the adverse CNS and emetic effects associated with prior PDE4 inhibitors.

Obviously, many modifications and variations of the invention as hereinbefore set forth can be made without departing from the spirit and scope thereof and, therefore, only such limitations should be imposed as are indicated by the appended claims.

What is claimed is:

1. A method of treating a mammal having an arthritic disease comprising administering to said mammal a therapeutically effective amount of a pharmaceutical composition comprising a compound having a formula

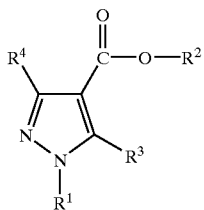

wherein
$R^1$ is optionally substituted aryl,
$R^2$ is selected from the group consisting of optionally substituted alkyl and aryl;
$R^3$ and $R^4$ are alkyl,
a pharmaceutically acceptable carrier, and,
optionally, a second antiinflammatory therapeutic agent.

2. The method of claim 1 wherein $R^1$ is phenyl, optionally substituted.

3. The method of claim 1 wherein $R^2$ is selected from the group consisting of ethyl, methyl, and

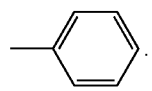

4. The method of claim 1 wherein $R^1$ is phenyl, optionally substituted; $R^2$ is ethyl; and $R^3$ and $R^4$ are methyl.

5. The method of claim 1 wherein the compound is selected from the group consisting of:
1-(4-bromophenyl)-3,5-dimethyl-1H-pyrazole-4-carboxylic acid ethyl ester;
3,5-dimethyl-1-(3-nitrophenyl)-1H-pyrazole-4-carboxylic acid ethyl ester;
3,5-dimethyl-1-phenyl-1H-pyrazole-4-carboxylic acid ethyl ester;
3,5-dimethyl-1-p-tolyl-1H-pyrazole-4-carboxylic acid ethyl ester;
3,5-dimethyl-1-(2-nitrophenyl)-1H-pyrazole-4-carboxylic acid ethyl ester;
3,5-dimethyl-1-(2-aminophenyl)-1H-pyrazole-4-carboxylic acid ethyl ester;
1-(3-aminophenyl)-3,5-dimethyl-1H-pyrazole-4-carboxylic acid ethyl ester;
3,5-dimethyl-1-(4-aminophenyl)-1H-pyrazole-4-carboxylic acid ethyl ester;
1-(4-aminophenyl)-3,5-dimethyl-1H-pyrazole-4-carboxylic acid;
1-(3-chlorophenyl)-3,5-dimethyl-1H-pyrazole-4-carboxylic acid ethyl ester;
3,5-dimethyl-1-m-tolyl-1H-pyrazole-4-carboxylic acid ethyl ester;
1-(3-fluorophenyl)-3,5-dimethyl-1H-pyrazole-4-carboxylic acid ethyl ester;
1-(3-methoxyphenyl)-3,5-dimethyl-1H-pyrazole-4-carboxylic acid ethyl ester;
1-(3-bromophenyl)-3,5-dimethyl-1H-pyrazole-4-carboxylic acid ethyl ester; and
1-(4-aminophenyl)-5-trifluoromethyl-1H-pyrazole-4-carboxylic acid ethyl ester.

6. The method of claim 1 wherein the compound is selected from the group consisting of:
3,5-dimethyl-1-(3-nitrophenyl)-1H-pyrazole-4-carboxylic acid ethyl ester;
3,5-dimethyl-1-phenyl-1H-pyrazole-4-carboxylic acid ethyl ester;
3,5-dimethyl-1-(2-aminophenyl)-1H-pyrazole-4-carboxylic acid ethyl ester;
3,5-dimethyl-1-(2-nitrophenyl)-1H-pyrazole-4-carboxylic acid ethyl ester;
1-(3-aminophenyl)-3,5-dimethyl-1H-pyrazole-4-carboxylic acid ethyl ester; and
3,5-dimethyl-1-(4-aminophenyl)-1H-pyrazole-4-carboxylic acid ethyl ester.

7. The method of claim 1 wherein the condition is rheumatoid arthritis, osteoarthritis, gouty arthritis, or spondylitis.

8. The method of claim 1 wherein the mammal is free of an emetic response.

9. A The method of claim 7 wherein the mammal exhibits minimal emetic response.

10. The method of claim 1 wherein the mammal exhibits minimal adverse central nervous system side effects.

11. The method of claim 1 wherein the mammal is free of adverse central nervous system side effects.

12. The method of claim 1 wherein the second antiinflammatory therapeutic agent is capable of targeting TNFα.

13. The method of claim 1 wherein the compound has a structure

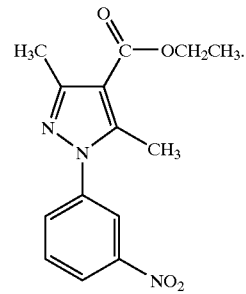

* * * * *

UNITED STATES PATENT AND TRADEMARK OFFICE
CERTIFICATE OF CORRECTION

PATENT NO.   : 6,569,885 B1
DATED        : May 27, 2003
INVENTOR(S)  : Timothy J. Martins et al.

It is certified that error appears in the above-identified patent and that said Letters Patent is hereby corrected as shown below:

<u>Column 55,</u>
Line 30, "optionally substituted aryl," should be -- optionally substituted aryl; --
Line 34, "$R^3$ and $R^4$ are alkyl," should be -- $R^3$ and $R^4$ are alkyl; --

<u>Column 56,</u>
Line 61, insert a period at the end of claim 13

Signed and Sealed this

Fifteenth Day of June, 2004

JON W. DUDAS
*Acting Director of the United States Patent and Trademark Office*